US010836815B2

(12) United States Patent
Wang et al.

(10) Patent No.: US 10,836,815 B2
(45) Date of Patent: Nov. 17, 2020

(54) **GENERATION AND COMPARATIVE KINETIC ANALYSIS OF NEW GLYCOSYNTHASE MUTANTS FROM *STREPTOCOCCUS PYOGENES* ENDOGLYCOSIDASES FOR ANTIBODY GLYCOENGINEERING**

(71) Applicant: UNIVERSITY OF MARYLAND, COLLEGE PARK, Waldorf, MD (US)

(72) Inventors: Lai-Xi Wang, Ellicott City, MD (US); Xin Tong, College Park, MD (US); Tiezheng Li, Columbia, MD (US)

(73) Assignee: UNIVERSITY OF MARYLAND, COLLEGE PARK, Waldorf, MD (US)

( * ) Notice: Subject to any disclaimer, the term of this patent is extended or adjusted under 35 U.S.C. 154(b) by 21 days.

(21) Appl. No.: 16/023,479

(22) Filed: Jun. 29, 2018

(65) Prior Publication Data

US 2019/0002945 A1    Jan. 3, 2019

Related U.S. Application Data

(60) Provisional application No. 62/526,635, filed on Jun. 29, 2017.

(51) Int. Cl.
| | | |
|---|---|---|
| *C07K 16/18* | (2006.01) | |
| *C12R 1/46* | (2006.01) | |
| *C07K 1/04* | (2006.01) | |
| *C07K 1/36* | (2006.01) | |
| *C07K 1/02* | (2006.01) | |
| *C07K 1/107* | (2006.01) | |
| *A61K 47/61* | (2017.01) | |
| *A61K 47/54* | (2017.01) | |
| *A61K 47/68* | (2017.01) | |
| *C07K 16/28* | (2006.01) | |
| *C07K 16/32* | (2006.01) | |
| *C12N 9/24* | (2006.01) | |
| *C12P 21/00* | (2006.01) | |
| *A61K 9/00* | (2006.01) | |

(52) U.S. Cl.
CPC ............ *C07K 16/18* (2013.01); *A61K 47/549* (2017.08); *A61K 47/61* (2017.08); *A61K 47/6803* (2017.08); *C07K 1/02* (2013.01); *C07K 1/045* (2013.01); *C07K 1/1077* (2013.01); *C07K 1/36* (2013.01); *C07K 16/2887* (2013.01); *C07K 16/32* (2013.01); *C12N 9/2402* (2013.01); *C12P 21/005* (2013.01); *C12R 1/46* (2013.01); *A61K 9/0019* (2013.01); *C07K 2317/10* (2013.01); *C07K 2317/24* (2013.01); *C07K 2317/41* (2013.01); *C12Y 302/01096* (2013.01)

(58) Field of Classification Search
None
See application file for complete search history.

(56) References Cited

U.S. PATENT DOCUMENTS

| | | | |
|---|---|---|---|
| 7,524,821 B2 | 4/2009 | Wang et al. | |
| 7,556,809 B2 | 7/2009 | Wang | |
| 7,604,804 B2 | 10/2009 | Wang et al. | |
| 7,728,106 B2 | 6/2010 | Wang | |
| 7,807,405 B2 | 10/2010 | Wang | |
| 8,354,247 B2 | 1/2013 | Wang | |
| 8,900,826 B2 | 12/2014 | Wang | |
| 9,175,326 B2 | 11/2015 | Wang | |
| 9,434,786 B2 | 9/2016 | Wang et al. | |
| 9,605,050 B2 | 3/2017 | Wang | |
| 9,845,360 B2 | 12/2017 | Wang et al. | |
| 9,850,473 B2 | 12/2017 | Wang | |
| 10,344,063 B2* | 7/2019 | Wang ................... | C07K 14/473 |
| 2015/0087814 A1 | 3/2015 | Wang et al. | |
| 2015/0176045 A1 | 6/2015 | Marcel et al. | |
| 2019/0002542 A1 | 1/2019 | Wang et al. | |
| 2019/0002945 A1 | 1/2019 | Wang et al. | |

FOREIGN PATENT DOCUMENTS

WO    WO2015057066    4/2015

OTHER PUBLICATIONS

Aikawa, J. et al. Trimming of glucosylated N-glycans by human ER alpha1,2-mannosidase I, *J Biochem* (2014), 155:375-384.
Arnold. J. N. et al. The Impact of Glycosylation on the Biological Function and Structure of Human Immunoglobulins, *Annu. Rev. Immunol.* (2007) 25:21-50.
Bhati, M. et al. Efficacy and safety of an anti-CD20 monoclonal antibody (Reditux) for the treatment of patients with moderate to severe rheumatoid arthritis following the failure of conventional synthetic disease-modifying anti-rheumatic drugs, *Clin Rheumatol* (2016), 35:1931-1935.
Bodnar, J. et al. Enzymatic removal of N-glycans by PNGase F coated magnetic microparticles, *Electrophoresis* (2016) 37:1264-1269.
Cao, K. et al. Monoclonal antibodies targeting non-small cell lung cancer stem-like cells by multipotent cancer stem cell monoclonal antibody library, *Int J Oncol* (2017), 50:587-596.
Campbell, I. K. et al. Therapeutic effect of IVIG on inflammatory arthritis in mice is dependent on the Fc portion and independent of sialylation or basophils, *J Immunol* (2014), 192: 5031-5038.
Cox, K. M. et al. Glycan optimization of a human monoclonal antibody in the aquatic plant Lemna minor. *Nat. Biotechnol.* (2006) 24:1591-1597.

(Continued)

*Primary Examiner* — Kagnew H Gebreyesus
(74) *Attorney, Agent, or Firm* — Marianne Fuierer; Olive Law Group, PLLC

(57) ABSTRACT

The present invention provides for recombinant Endo-S mutants (named Endo-S glycosynthases) that exhibit reduced hydrolysis activity and increased transglycosylation activity for the synthesis of glycoproteins wherein a desired sugar chain is added to a fucosylated or nonfucosylated GlcNAc-IgG acceptor. As such, the present invention allows for the synthesis and remodeling of therapeutic antibodies thereby providing for certain biological activities, such as, prolonged half-life time in vivo, less immunogenicity, enhanced in vivo activity, increased targeting ability, and/or ability to deliver a therapeutic agent.

10 Claims, 4 Drawing Sheets

Specification includes a Sequence Listing.

(56) References Cited

OTHER PUBLICATIONS

Damen, C. W. et al. Electrospray ionization quadrupole ion-mobility time-of-flight mass spectrometry as a tool to distinguish the lot-to-lot heterogeneity in N-glycosylation profile of the therapeutic monoclonal antibody trastuzumab, *J Am Soc Mass Spectrom* (2009), 20:2021-2033.

Danan, L. M. et al. Mass spectrometric kinetic analysis of human tyrosylprotein sulfotransferase-1 and -2, *J Am Soc Mass Spectrom* (2008), 19:1459-1466.

Elvin, J. G. et al. Therapeutic antibodies: market considerations, disease targets and bioprocessing, *Int J Pharm* (2013), 440:83-98.

Ge, X. et al. A strategy for the determination of enzyme kinetics using electrospray ionization with an ion trap mass spectrometer, *Anal Chem* (2001) 73:5078-5082.

Giddens, J. P. et al. Endo-F3 Glycosynthase Mutants Enable Chemoenzymatic Synthesis of Core-fucosylated Triantennary Complex Type Glycopeptides and Glycoproteins. *J. Biol. Chem.* (2016) 291:9356-9370.

Huang, W. et al. Chemoenzymatic glycoengineering of intact IgG antibodies for gain of functions. *J. Am. Chem. Soc.* (2012) 134:12308-12318.

Illidge, T. et al. Update on obinutuzumab in the treatment of B-cell malignancies. *Expert Opin. Biol. Ther.* (2014) 14:1507-1517.

Kurogochi, M. et al. Glycoengineered Monoclonal Antibodies with Homogeneous Glycan (M3, G0, G2, and A2) Using a Chemoenzymatic Approach Have Different Affinities for FcgammaRIIIa and Variable Antibody-Dependent Cellular Cytotoxicity Activities. *PLoS One* (2015) 10:e0132848.

Li, T. et al. Glycosynthase mutants of endoglycosidase S2 show potent transglycosylation activity and remarkably relaxed substrate specificity for antibody glycosylation remodeling, *Journal of Biological Chemistry*, (2016) 291(32):16508-16518.

Li, W. et al. Core fucosylation of IgG B cell receptor is required for antigen recognition and antibody production, *J Immunol* (2015), 194:2596-2606.

Lin, C. W. et al. A common glycan structure on immunoglobulin G for enhancement of effector functions. *Proc. Natl. Acad. Sci. USA* (2015) 112:10611-10616.

Liu, R. et al. Evaluation of a glycoengineered monoclonal antibody via LC-MS analysis in combination with multiple enzymatic digestion. *MAbs* (2016) 8:340-346.

Niwa, R. et al. Defucosylated chimeric anti-CC chemokine receptor 4 IgG1 with enhanced antibody-dependent cellular cytotoxicity shows potent therapeutic activity to T-cell leukemia and lymphoma. *Cancer Res.* (2004) 64:2127-2133.

Olivova, P. et al. Determination of N-glycosylation sites and site heterogeneity in a monoclonal antibody by electrospray quadrupole ion-mobility time-of-flight mass spectrometry, *Rapid Commun Mass Spectrom* (2008), 22:29-40.

Parsons, T. B. Optimal Synthetic Glycosylation of a Therapeutic Antibody. *Angew. Chem. Int. Ed.* (2016) 55:2361-2367.

Peipp, M. et al. Antibody fucosylation differentially impacts cytotoxicity mediated by NK and PMN effector cells, *Blood* (2008) 112:2390-2399.

Pi, N. et al. Kinetic analysis of NodST sulfotransferase using an electrospray ionization mass spectrometry assay, *Biochemistry* (2002) 41:13283-13288.

Scallon, B. et al. Quantitative in vivo comparisons of the Fc gamma receptor-dependent agonist activities of different fucosylation variants of an immunoglobulin G antibody, *Int Immunopharmacol* (2007) 7:761-772.

Sjorgren, J. et al. EndoS and EndoS2 hydrolyze Fc-glycans on therapeutic antibodies with different glycoform selectivity and can be used for rapid quantification of high-mannose glycans. *Glycobiology* (2015) 25:1053-1063.

Stanley, P. et al. Molecular analysis of three gain-of-function CHO mutants that add the bisecting GlcNAc to N-glycans. *Glycobiology* (2005) 15:43-53.

Schwab, I. et al. Role of sialylation in the anti-inflammatory activity of intravenous immunoglobulin—F(ab')$_2$ versus Fc sialylation, *Clin. Exp. Immunol. Suppl 1* (2014), 178:97-99.

Tong, X. et al. One-pot enzymatic glycan remodeling of a therapeutic monoclonal antibody by endoglycosidase S (Endo-S) from *Streptococcus pyogenes, Bioorg Med Chem* (2018), 26:1347-1355.

Trastoy, B. et al. Crystal structure of *Streptococcus pyogenes* EndoS, an immunomodulatory endoglycosidase specific for human IgG antibodies, *Proc Natl Acad Sci USA* (2014), 111:6714-6719.

Trastoy, B. et al. Structural basis for the recognition of complex-type N-glycans by Endoglycosidase S, *Nat Commun* (2018) 9:1874.

Washburn, N. et al. Controlled tetra-Fc sialylation of IVIg results in a drug candidate with consistent enhanced anti-inflammatory activity. *Proc. Natl. Acad. Sci. USA* (2015) 112:E1297-1306.

Wei, Y. et al. Glycoengineering of human IgG1-Fc through combined yeast expression and in vitro chemoenzymatic glycosylation. *Biochemistry* (2008) 47:10294-10304.

Yamane-Ohnuki, N. Establishment of FUT8 knockout Chinese hamster ovary cells: an ideal host cell line for producing completely defucosylated antibodies with enhanced antibody-dependent cellular cytotoxicity. *Biotechnol. Bioeng.* (2004) 87: 614-622.

Zou, G. et al. Chemoenzymatic synthesis and Fcgamma receptor binding of homogeneous glycoforms of antibody Fc domain. Presence of a bisecting sugar moiety enhances the affinity of Fc to FcgammaIIIa receptor. *J. Am. Chem. Soc.* (2011) 133:18975-18991.

\* cited by examiner

SEQUENCE LISTING

<160> NUMBER OF SEQ ID NOS: 11

<210> SEQ ID NO 1
<211> LENGTH: 995
<212> TYPE: PRT
<213> ORGANISM: Streptococcus pyogenes

<400> SEQUENCE: 1

```
Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Val Gln Lys Gly Leu Pro
            35                  40                  45

Ser Ile Asp Ser Leu His Tyr Leu Ser Glu Asn Ser Lys Lys Glu Phe
        50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
                100                 105                 110

Leu Tyr Gly Gly Tyr Phe Arg Thr Trp His Asp Lys Thr Ser Asp Pro
            115                 120                 125

Thr Glu Lys Asp Lys Val Asn Ser Met Gly Glu Leu Pro Lys Glu Val
        130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
                180                 185                 190

Asn Ser Gly Ile Ala Glu Asp Thr Ser Lys Tyr Pro Asn Thr Pro Glu
            195                 200                 205

Gly Asn Lys Ala Leu Ala Lys Ala Ile Val Asp Glu Tyr Val Tyr Lys
        210                 215                 220

Tyr Asn Leu Asp Gly Leu Asp Val Asp Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
                260                 265                 270

Ser Arg Leu Phe Ile Met Asp Ser Thr Tyr Met Ala Asp Lys Asn Pro
            275                 280                 285

Leu Ile Glu Arg Gly Ala Pro Tyr Ile Asn Leu Leu Val Gln Val
        290                 295                 300

Tyr Gly Ser Gln Gly Glu Lys Gly Gly Trp Glu Pro Val Ser Asn Arg
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Tyr Glu Glu Asn Ala
                340                 345                 350

Gln Glu Gly Asn Leu Trp Tyr Asp Ile Asn Ser Arg Lys Asp Glu Asp
            355                 360                 365
```

-continued

Lys Ala Asn Gly Ile Asn Thr Asp Ile Thr Gly Thr Arg Ala Glu Arg
    370                 375                 380

Tyr Ala Arg Trp Gln Pro Lys Thr Gly Val Lys Gly Gly Ile Phe
385                 390                 395                 400

Ser Tyr Ala Ile Asp Arg Asp Gly Val Ala His Gln Pro Lys Lys Tyr
                405                 410                 415

Ala Lys Gln Lys Glu Phe Lys Asp Ala Thr Asp Asn Ile Phe His Ser
                420                 425                 430

Asp Tyr Ser Val Ser Lys Ala Leu Lys Thr Val Met Leu Lys Asp Lys
            435                 440                 445

Ser Tyr Asp Leu Ile Asp Glu Lys Asp Phe Pro Asp Lys Ala Leu Arg
        450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
                500                 505                 510

Ser Arg Ile Thr Lys Leu Asp Arg Ser Val Leu Pro Ala Asn Met Lys
            515                 520                 525

Pro Gly Lys Asp Thr Leu Glu Thr Val Leu Glu Thr Tyr Lys Lys Asp
        530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
                565                 570                 575

Thr Leu Ala Gly Leu Asp Ala Ala Thr Leu Thr Ser Leu Glu Lys Val
                580                 585                 590

Asp Ile Ser Gly Asn Lys Leu Asp Leu Ala Pro Gly Thr Glu Asn Arg
            595                 600                 605

Gln Ile Phe Asp Thr Met Leu Ser Thr Ile Ser Asn His Val Gly Ser
        610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
                645                 650                 655

Lys Val Asp Leu Gln Ser Gln Leu Leu Phe Gly Val Thr Asn Gln
                660                 665                 670

Gly Thr Leu Ile Asn Ser Glu Ala Asp Tyr Lys Ala Tyr Gln Asn His
            675                 680                 685

Lys Ile Ala Gly Arg Ser Phe Val Asp Ser Asn Tyr His Tyr Asn Asn
        690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
                725                 730                 735

Tyr Lys Val Asp Phe Phe Ser Pro Ala Asp Lys Thr Lys Ala Val His
                740                 745                 750

Thr Ala Lys Val Ile Val Gly Asp Glu Lys Thr Met Met Val Asn Leu
            755                 760                 765

Ala Glu Gly Ala Thr Val Ile Gly Gly Ser Ala Asp Pro Val Asn Ala
        770                 775                 780

Arg Lys Val Phe Asp Gly Gln Leu Gly Ser Glu Thr Asp Asn Ile Ser

```
              785                 790                 795                 800
Leu Gly Trp Asp Ser Lys Gln Ser Ile Ile Phe Lys Leu Lys Glu Asp
                805                 810                 815
Gly Leu Ile Lys His Trp Arg Phe Phe Asn Asp Ser Ala Arg Asn Pro
                820                 825                 830
Glu Thr Thr Asn Lys Pro Ile Gln Glu Ala Ser Leu Gln Ile Phe Asn
                835                 840                 845
Ile Lys Asp Tyr Asn Leu Asp Asn Leu Leu Glu Asn Pro Asn Lys Phe
        850                 855                 860
Asp Asp Glu Lys Tyr Trp Ile Thr Val Asp Thr Tyr Ser Ala Gln Gly
865                 870                 875                 880
Glu Arg Ala Thr Ala Phe Ser Asn Thr Leu Asn Asn Ile Thr Ser Lys
                885                 890                 895
Tyr Trp Arg Val Val Phe Asp Thr Lys Gly Asp Arg Tyr Ser Ser Pro
                900                 905                 910
Val Val Pro Glu Leu Gln Ile Leu Gly Tyr Pro Leu Pro Asn Ala Asp
                915                 920                 925
Thr Ile Met Lys Thr Val Thr Thr Ala Lys Glu Leu Ser Gln Gln Lys
                930                 935                 940
Asp Lys Phe Ser Gln Lys Met Leu Asp Glu Leu Lys Ile Lys Glu Met
945                 950                 955                 960
Ala Leu Glu Thr Ser Leu Asn Ser Lys Ile Phe Asp Val Thr Ala Ile
                965                 970                 975
Asn Ala Asn Ala Gly Val Leu Lys Asp Cys Ile Glu Lys Arg Gln Leu
                980                 985                 990
Leu Lys Lys
        995

<210> SEQ ID NO 2
<211> LENGTH: 995
<212> TYPE: PRT
<213> ORGANISM: Artificial Sequence
<220> FEATURE:
<223> OTHER INFORMATION: Synthetic Construct

<400> SEQUENCE: 2

Met Asp Lys His Leu Leu Val Lys Arg Thr Leu Gly Cys Val Cys Ala
1               5                   10                  15
Ala Thr Leu Met Gly Ala Ala Leu Ala Thr His His Asp Ser Leu Asn
                20                  25                  30
Thr Val Lys Ala Glu Glu Lys Thr Val Gln Val Gln Lys Gly Leu Pro
        35                  40                  45
Ser Ile Asp Ser Leu His Tyr Leu Ser Glu Asn Ser Lys Lys Glu Phe
    50                  55                  60
Lys Glu Glu Leu Ser Lys Ala Gly Gln Glu Ser Gln Lys Val Lys Glu
65                  70                  75                  80
Ile Leu Ala Lys Ala Gln Gln Ala Asp Lys Gln Ala Gln Glu Leu Ala
                85                  90                  95
Lys Met Lys Ile Pro Glu Lys Ile Pro Met Lys Pro Leu His Gly Pro
                100                 105                 110
Leu Tyr Gly Gly Tyr Phe Arg Thr Trp His Asp Lys Thr Ser Asp Pro
        115                 120                 125
Thr Glu Lys Asp Lys Val Asn Ser Met Gly Glu Leu Pro Lys Glu Val
    130                 135                 140
Asp Leu Ala Phe Ile Phe His Asp Trp Thr Lys Asp Tyr Ser Leu Phe
```

```
                145                 150                 155                 160
Trp Lys Glu Leu Ala Thr Lys His Val Pro Lys Leu Asn Lys Gln Gly
                    165                 170                 175
Thr Arg Val Ile Arg Thr Ile Pro Trp Arg Phe Leu Ala Gly Gly Asp
                    180                 185                 190
Asn Ser Gly Ile Ala Glu Asp Thr Ser Lys Tyr Pro Asn Thr Pro Glu
                    195                 200                 205
Gly Asn Lys Ala Leu Ala Lys Ala Ile Val Asp Glu Tyr Val Tyr Lys
        210                 215                 220
Tyr Asn Leu Asp Gly Leu Asp Val Met Val Glu His Asp Ser Ile Pro
225                 230                 235                 240
Lys Val Asp Lys Lys Glu Asp Thr Ala Gly Val Glu Arg Ser Ile Gln
                    245                 250                 255
Val Phe Glu Glu Ile Gly Lys Leu Ile Gly Pro Lys Gly Val Asp Lys
                    260                 265                 270
Ser Arg Leu Phe Ile Met Asp Ser Thr Tyr Met Ala Asp Lys Asn Pro
        275                 280                 285
Leu Ile Glu Arg Gly Ala Pro Tyr Ile Asn Leu Leu Leu Val Gln Val
        290                 295                 300
Tyr Gly Ser Gln Gly Glu Lys Gly Gly Trp Glu Pro Val Ser Asn Arg
305                 310                 315                 320
Pro Glu Lys Thr Met Glu Glu Arg Trp Gln Gly Tyr Ser Lys Tyr Ile
                    325                 330                 335
Arg Pro Glu Gln Tyr Met Ile Gly Phe Ser Phe Tyr Glu Glu Asn Ala
                    340                 345                 350
Gln Glu Gly Asn Leu Trp Tyr Asp Ile Asn Ser Arg Lys Asp Glu Asp
                355                 360                 365
Lys Ala Asn Gly Ile Asn Thr Asp Ile Thr Gly Thr Arg Ala Glu Arg
        370                 375                 380
Tyr Ala Arg Trp Gln Pro Lys Thr Gly Gly Val Lys Gly Gly Ile Phe
385                 390                 395                 400
Ser Tyr Ala Ile Asp Arg Asp Gly Val Ala His Gln Pro Lys Lys Tyr
                    405                 410                 415
Ala Lys Gln Lys Glu Phe Lys Asp Ala Thr Asp Asn Ile Phe His Ser
                    420                 425                 430
Asp Tyr Ser Val Ser Lys Ala Leu Lys Thr Val Met Leu Lys Asp Lys
                435                 440                 445
Ser Tyr Asp Leu Ile Asp Glu Lys Asp Phe Pro Asp Lys Ala Leu Arg
        450                 455                 460
Glu Ala Val Met Ala Gln Val Gly Thr Arg Lys Gly Asp Leu Glu Arg
465                 470                 475                 480
Phe Asn Gly Thr Leu Arg Leu Asp Asn Pro Ala Ile Gln Ser Leu Glu
                    485                 490                 495
Gly Leu Asn Lys Phe Lys Lys Leu Ala Gln Leu Asp Leu Ile Gly Leu
                    500                 505                 510
Ser Arg Ile Thr Lys Leu Asp Arg Ser Val Leu Pro Ala Asn Met Lys
        515                 520                 525
Pro Gly Lys Asp Thr Leu Glu Thr Val Leu Glu Thr Tyr Lys Lys Asp
        530                 535                 540
Asn Lys Glu Glu Pro Ala Thr Ile Pro Pro Val Ser Leu Lys Val Ser
545                 550                 555                 560
Gly Leu Thr Gly Leu Lys Glu Leu Asp Leu Ser Gly Phe Asp Arg Glu
                    565                 570                 575
```

```
Thr Leu Ala Gly Leu Asp Ala Ala Thr Leu Thr Ser Leu Glu Lys Val
            580                 585                 590

Asp Ile Ser Gly Asn Lys Leu Asp Leu Ala Pro Gly Thr Glu Asn Arg
        595                 600                 605

Gln Ile Phe Asp Thr Met Leu Ser Thr Ile Ser Asn His Val Gly Ser
610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
                645                 650                 655

Lys Val Asp Leu Gln Ser Gln Leu Leu Phe Gly Thr Val Thr Asn Gln
            660                 665                 670

Gly Thr Leu Ile Asn Ser Glu Ala Asp Tyr Lys Ala Tyr Gln Asn His
        675                 680                 685

Lys Ile Ala Gly Arg Ser Phe Val Asp Ser Asn Tyr His Tyr Asn Asn
690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
                725                 730                 735

Tyr Lys Val Asp Phe Phe Ser Pro Ala Asp Lys Thr Lys Ala Val His
            740                 745                 750

Thr Ala Lys Val Ile Val Gly Asp Glu Lys Thr Met Met Val Asn Leu
        755                 760                 765

Ala Glu Gly Ala Thr Val Ile Gly Gly Ser Ala Asp Pro Val Asn Ala
770                 775                 780

Arg Lys Val Phe Asp Gly Gln Leu Gly Ser Glu Thr Asp Asn Ile Ser
785                 790                 795                 800

Leu Gly Trp Asp Ser Lys Gln Ser Ile Ile Phe Lys Leu Lys Glu Asp
                805                 810                 815

Gly Leu Ile Lys His Trp Arg Phe Phe Asn Asp Ser Ala Arg Asn Pro
            820                 825                 830

Glu Thr Thr Asn Lys Pro Ile Gln Glu Ala Ser Leu Gln Ile Phe Asn
        835                 840                 845

Ile Lys Asp Tyr Asn Leu Asp Asn Leu Leu Glu Asn Pro Asn Lys Phe
850                 855                 860

Asp Asp Glu Lys Tyr Trp Ile Thr Val Asp Thr Tyr Ser Ala Gln Gly
865                 870                 875                 880

Glu Arg Ala Thr Ala Phe Ser Asn Thr Leu Asn Asn Ile Thr Ser Lys
                885                 890                 895

Tyr Trp Arg Val Val Phe Asp Thr Lys Gly Asp Arg Tyr Ser Ser Pro
            900                 905                 910

Val Val Pro Glu Leu Gln Ile Leu Gly Tyr Pro Leu Pro Asn Ala Asp
        915                 920                 925

Thr Ile Met Lys Thr Val Thr Thr Ala Lys Glu Leu Ser Gln Gln Lys
930                 935                 940

Asp Lys Phe Ser Gln Lys Met Leu Asp Glu Leu Lys Ile Lys Glu Met
945                 950                 955                 960

Ala Leu Glu Thr Ser Leu Asn Ser Lys Ile Phe Asp Val Thr Ala Ile
                965                 970                 975

Asn Ala Asn Ala Gly Val Leu Lys Asp Cys Ile Glu Lys Arg Gln Leu
            980                 985                 990
```

Leu Lys Lys
        995

<210> SEQ ID NO 3
<211> LENGTH: 995
<212> TYPE: PRT
<213> ORGANISM: Artificial Sequence
<220> FEATURE:
<223> OTHER INFORMATION: Synthetic Construct

<400> SEQUENCE: 3

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Val Gln Lys Gly Leu Pro
        35                  40                  45

Ser Ile Asp Ser Leu His Tyr Leu Ser Glu Asn Ser Lys Lys Glu Phe
    50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
            100                 105                 110

Leu Tyr Gly Gly Tyr Phe Arg Thr Trp His Asp Lys Thr Ser Asp Pro
        115                 120                 125

Thr Glu Lys Asp Lys Val Asn Ser Met Gly Glu Leu Pro Lys Glu Val
    130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
            180                 185                 190

Asn Ser Gly Ile Ala Glu Asp Thr Ser Lys Tyr Pro Asn Thr Pro Glu
        195                 200                 205

Gly Asn Lys Ala Leu Ala Lys Ala Ile Val Asp Glu Tyr Val Tyr Lys
    210                 215                 220

Tyr Asn Leu Asp Gly Leu Asp Val Gln Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
            260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Gln Val
    290                 295                 300

Tyr Gly Ser Gln Gly Glu Lys Gly Gly Trp Glu Pro Val Ser Asn Arg
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Tyr Glu Glu Asn Ala
            340                 345                 350

-continued

Gln Glu Gly Asn Leu Trp Tyr Asp Ile Asn Ser Arg Lys Asp Glu Asp
            355                 360                 365

Lys Ala Asn Gly Ile Asn Thr Asp Ile Thr Gly Thr Arg Ala Glu Arg
370                 375                 380

Tyr Ala Arg Trp Gln Pro Lys Thr Gly Gly Val Lys Gly Gly Ile Phe
385                 390                 395                 400

Ser Tyr Ala Ile Asp Arg Asp Gly Val Ala His Gln Pro Lys Lys Tyr
            405                 410                 415

Ala Lys Gln Lys Glu Phe Lys Asp Ala Thr Asp Asn Ile Phe His Ser
            420                 425                 430

Asp Tyr Ser Val Ser Lys Ala Leu Lys Thr Val Met Leu Lys Asp Lys
            435                 440                 445

Ser Tyr Asp Leu Ile Asp Glu Lys Asp Phe Pro Asp Lys Ala Leu Arg
            450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
            485                 490                 495

Gly Leu Asn Lys Phe Lys Lys Leu Ala Gln Leu Asp Leu Ile Gly Leu
            500                 505                 510

Ser Arg Ile Thr Lys Leu Asp Arg Ser Val Leu Pro Ala Asn Met Lys
            515                 520                 525

Pro Gly Lys Asp Thr Leu Glu Thr Val Leu Glu Thr Tyr Lys Lys Asp
            530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
            565                 570                 575

Thr Leu Ala Gly Leu Asp Ala Ala Thr Leu Thr Ser Leu Glu Lys Val
            580                 585                 590

Asp Ile Ser Gly Asn Lys Leu Asp Leu Ala Pro Gly Thr Glu Asn Arg
            595                 600                 605

Gln Ile Phe Asp Thr Met Leu Ser Thr Ile Ser Asn His Val Gly Ser
610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
            645                 650                 655

Lys Val Asp Leu Gln Ser Gln Leu Leu Phe Gly Thr Val Thr Asn Gln
            660                 665                 670

Gly Thr Leu Ile Asn Ser Glu Ala Asp Tyr Lys Ala Tyr Gln Asn His
            675                 680                 685

Lys Ile Ala Gly Arg Ser Phe Val Asp Ser Asn Tyr His Tyr Asn Asn
            690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
            725                 730                 735

Tyr Lys Val Asp Phe Phe Ser Pro Ala Asp Lys Thr Lys Ala Val His
            740                 745                 750

Thr Ala Lys Val Ile Val Gly Asp Glu Lys Thr Met Met Val Asn Leu
            755                 760                 765

Ala Glu Gly Ala Thr Val Ile Gly Gly Ser Ala Asp Pro Val Asn Ala

```
                770                 775                 780
Arg Lys Val Phe Asp Gly Gln Leu Gly Ser Glu Thr Asp Asn Ile Ser
785                 790                 795                 800

Leu Gly Trp Asp Ser Lys Gln Ser Ile Ile Phe Lys Leu Lys Glu Asp
                805                 810                 815

Gly Leu Ile Lys His Trp Arg Phe Phe Asn Asp Ser Ala Arg Asn Pro
                820                 825                 830

Glu Thr Thr Asn Lys Pro Ile Gln Glu Ala Ser Leu Gln Ile Phe Asn
                835                 840                 845

Ile Lys Asp Tyr Asn Leu Asp Asn Leu Leu Glu Asn Pro Asn Lys Phe
                850                 855                 860

Asp Asp Glu Lys Tyr Trp Ile Thr Val Asp Thr Tyr Ser Ala Gln Gly
865                 870                 875                 880

Glu Arg Ala Thr Ala Phe Ser Asn Thr Leu Asn Asn Ile Thr Ser Lys
                885                 890                 895

Tyr Trp Arg Val Val Phe Asp Thr Lys Gly Asp Arg Tyr Ser Ser Pro
                900                 905                 910

Val Val Pro Glu Leu Gln Ile Leu Gly Tyr Pro Leu Pro Asn Ala Asp
                915                 920                 925

Thr Ile Met Lys Thr Val Thr Thr Ala Lys Glu Leu Ser Gln Gln Lys
                930                 935                 940

Asp Lys Phe Ser Gln Lys Met Leu Asp Glu Leu Lys Ile Lys Glu Met
945                 950                 955                 960

Ala Leu Glu Thr Ser Leu Asn Ser Lys Ile Phe Asp Val Thr Ala Ile
                965                 970                 975

Asn Ala Asn Ala Gly Val Leu Lys Asp Cys Ile Glu Lys Arg Gln Leu
                980                 985                 990

Leu Lys Lys
       995

<210> SEQ ID NO 4
<211> LENGTH: 995
<212> TYPE: PRT
<213> ORGANISM: Artificial Sequence
<220> FEATURE:
<223> OTHER INFORMATION: Synthetic Construct

<400> SEQUENCE: 4

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Val Gln Lys Gly Leu Pro
                35                  40                  45

Ser Ile Asp Ser Leu His Tyr Leu Ser Glu Asn Ser Lys Lys Glu Phe
50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
                100                 105                 110

Leu Tyr Gly Gly Tyr Phe Arg Thr Trp His Asp Lys Thr Ser Asp Pro
                115                 120                 125

Thr Glu Lys Asp Lys Val Asn Ser Met Gly Glu Leu Pro Lys Glu Val
```

-continued

```
            130                 135                 140
Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
            180                 185                 190

Asn Ser Gly Ile Ala Glu Asp Thr Ser Lys Tyr Pro Asn Thr Pro Glu
                195                 200                 205

Gly Asn Lys Ala Leu Ala Lys Ala Ile Val Asp Glu Tyr Val Tyr Lys
            210                 215                 220

Tyr Asn Leu Asp Gly Leu Asp Val Ala Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
                260                 265                 270

Ser Arg Leu Phe Ile Met Asp Ser Thr Tyr Met Ala Asp Lys Asn Pro
            275                 280                 285

Leu Ile Glu Arg Gly Ala Pro Tyr Ile Asn Leu Leu Leu Val Gln Val
            290                 295                 300

Tyr Gly Ser Gln Gly Glu Lys Gly Gly Trp Glu Pro Val Ser Asn Arg
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Tyr Glu Glu Asn Ala
                340                 345                 350

Gln Glu Gly Asn Leu Trp Tyr Asp Ile Asn Ser Arg Lys Asp Glu Asp
            355                 360                 365

Lys Ala Asn Gly Ile Asn Thr Asp Ile Thr Gly Thr Arg Ala Glu Arg
            370                 375                 380

Tyr Ala Arg Trp Gln Pro Lys Thr Gly Gly Val Lys Gly Gly Ile Phe
385                 390                 395                 400

Ser Tyr Ala Ile Asp Arg Asp Gly Val Ala His Gln Pro Lys Lys Tyr
                405                 410                 415

Ala Lys Gln Lys Glu Phe Lys Asp Ala Thr Asp Asn Ile Phe His Ser
                420                 425                 430

Asp Tyr Ser Val Ser Lys Ala Leu Lys Thr Val Met Leu Lys Asp Lys
            435                 440                 445

Ser Tyr Asp Leu Ile Asp Glu Lys Asp Phe Pro Asp Lys Ala Leu Arg
            450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
            500                 505                 510

Ser Arg Ile Thr Lys Leu Asp Arg Ser Val Leu Pro Ala Asn Met Lys
            515                 520                 525

Pro Gly Lys Asp Thr Leu Glu Thr Val Leu Thr Tyr Lys Lys Asp
            530                 535                 540

Asn Lys Glu Glu Pro Ala Thr Ile Pro Pro Val Ser Leu Lys Val Ser
545                 550                 555                 560
```

```
Gly Leu Thr Gly Leu Lys Glu Leu Asp Leu Ser Gly Phe Asp Arg Glu
                565                 570                 575

Thr Leu Ala Gly Leu Asp Ala Ala Thr Leu Thr Ser Leu Glu Lys Val
                580                 585                 590

Asp Ile Ser Gly Asn Lys Leu Asp Leu Ala Pro Gly Thr Glu Asn Arg
                595                 600                 605

Gln Ile Phe Asp Thr Met Leu Ser Thr Ile Ser Asn His Val Gly Ser
                610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
                645                 650                 655

Lys Val Asp Leu Gln Ser Gln Leu Leu Phe Gly Thr Val Thr Asn Gln
                660                 665                 670

Gly Thr Leu Ile Asn Ser Glu Ala Asp Tyr Lys Ala Tyr Gln Asn His
                675                 680                 685

Lys Ile Ala Gly Arg Ser Phe Val Asp Ser Asn Tyr His Tyr Asn Asn
690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Thr
                    725                 730                 735

Tyr Lys Val Asp Phe Phe Ser Pro Ala Asp Lys Thr Lys Ala Val His
                740                 745                 750

Thr Ala Lys Val Ile Val Gly Asp Glu Lys Thr Met Met Val Asn Leu
                755                 760                 765

Ala Glu Gly Ala Thr Val Ile Gly Gly Ser Ala Asp Pro Val Asn Ala
                770                 775                 780

Arg Lys Val Phe Asp Gly Gln Leu Gly Ser Glu Thr Asp Asn Ile Ser
785                 790                 795                 800

Leu Gly Trp Asp Ser Lys Gln Ser Ile Ile Phe Lys Leu Lys Glu Asp
                805                 810                 815

Gly Leu Ile Lys His Trp Arg Phe Phe Asn Asp Ser Ala Arg Asn Pro
                820                 825                 830

Glu Thr Thr Asn Lys Pro Ile Gln Glu Ala Ser Leu Gln Ile Phe Asn
                835                 840                 845

Ile Lys Asp Tyr Asn Leu Asp Asn Leu Leu Glu Asn Pro Asn Lys Phe
850                 855                 860

Asp Asp Glu Lys Tyr Trp Ile Thr Val Asp Thr Tyr Ser Ala Gln Gly
865                 870                 875                 880

Glu Arg Ala Thr Ala Phe Ser Asn Thr Leu Asn Asn Ile Thr Ser Lys
                885                 890                 895

Tyr Trp Arg Val Val Phe Asp Thr Lys Gly Asp Arg Tyr Ser Ser Pro
                900                 905                 910

Val Val Pro Glu Leu Gln Ile Leu Gly Tyr Pro Leu Pro Asn Ala Asp
                915                 920                 925

Thr Ile Met Lys Thr Val Thr Thr Ala Lys Glu Leu Ser Gln Gln Lys
                930                 935                 940

Asp Lys Phe Ser Gln Lys Met Leu Asp Glu Leu Lys Ile Lys Glu Met
945                 950                 955                 960

Ala Leu Glu Thr Ser Leu Asn Ser Lys Ile Phe Asp Val Thr Ala Ile
                965                 970                 975
```

Asn Ala Asn Ala Gly Val Leu Lys Asp Cys Ile Glu Lys Arg Gln Leu
            980                 985                 990

Leu Lys Lys
        995

<210> SEQ ID NO 5
<211> LENGTH: 995
<212> TYPE: PRT
<213> ORGANISM: Artificial Sequence
<220> FEATURE:
<223> OTHER INFORMATION: Synthetic Construct

<400> SEQUENCE: 5

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Val Gln Lys Gly Leu Pro
            35                  40                  45

Ser Ile Asp Ser Leu His Tyr Leu Ser Glu Asn Ser Lys Lys Glu Phe
        50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
            100                 105                 110

Leu Tyr Gly Gly Tyr Phe Arg Thr Trp His Asp Lys Thr Ser Asp Pro
        115                 120                 125

Thr Glu Lys Asp Lys Val Asn Ser Met Gly Glu Leu Pro Lys Glu Val
        130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
            180                 185                 190

Asn Ser Gly Ile Ala Glu Asp Thr Ser Lys Tyr Pro Asn Thr Pro Glu
        195                 200                 205

Gly Asn Lys Ala Leu Ala Lys Ala Ile Val Asp Glu Tyr Val Tyr Lys
    210                 215                 220

Tyr Asn Leu Asp Gly Leu Asp Val Cys Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
            260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Gln Val
    290                 295                 300

Tyr Gly Ser Gln Gly Glu Lys Gly Gly Trp Glu Pro Val Ser Asn Arg
305                 310                 315                 320

Pro Glu Lys Thr Met Glu Glu Arg Trp Gln Gly Tyr Ser Lys Tyr Ile
                325                 330                 335

-continued

Arg Pro Glu Gln Tyr Met Ile Gly Phe Ser Phe Tyr Glu Glu Asn Ala
                340                 345                 350

Gln Glu Gly Asn Leu Trp Tyr Asp Ile Asn Ser Arg Lys Asp Glu Asp
            355                 360                 365

Lys Ala Asn Gly Ile Asn Thr Asp Ile Thr Gly Thr Arg Ala Glu Arg
370                 375                 380

Tyr Ala Arg Trp Gln Pro Lys Thr Gly Gly Val Lys Gly Gly Ile Phe
385                 390                 395                 400

Ser Tyr Ala Ile Asp Arg Asp Gly Val Ala His Gln Pro Lys Lys Tyr
                405                 410                 415

Ala Lys Gln Lys Glu Phe Lys Asp Ala Thr Asp Asn Ile Phe His Ser
            420                 425                 430

Asp Tyr Ser Val Ser Lys Ala Leu Lys Thr Val Met Leu Lys Asp Lys
        435                 440                 445

Ser Tyr Asp Leu Ile Asp Glu Lys Asp Phe Pro Asp Lys Ala Leu Arg
    450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
            500                 505                 510

Ser Arg Ile Thr Lys Leu Asp Arg Ser Val Leu Pro Ala Asn Met Lys
        515                 520                 525

Pro Gly Lys Asp Thr Leu Glu Thr Val Leu Glu Thr Tyr Lys Lys Asp
    530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
                565                 570                 575

Thr Leu Ala Gly Leu Asp Ala Ala Thr Leu Thr Ser Leu Glu Lys Val
            580                 585                 590

Asp Ile Ser Gly Asn Lys Leu Asp Leu Ala Pro Gly Thr Glu Asn Arg
        595                 600                 605

Gln Ile Phe Asp Thr Met Leu Ser Thr Ile Ser Asn His Val Gly Ser
    610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
                645                 650                 655

Lys Val Asp Leu Gln Ser Gln Leu Leu Phe Gly Thr Val Thr Asn Gln
            660                 665                 670

Gly Thr Leu Ile Asn Ser Glu Ala Asp Tyr Lys Ala Tyr Gln Asn His
        675                 680                 685

Lys Ile Ala Gly Arg Ser Phe Val Asp Ser Asn Tyr His Tyr Asn Asn
    690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
                725                 730                 735

Tyr Lys Val Asp Phe Phe Ser Pro Ala Asp Lys Thr Lys Ala Val His
            740                 745                 750

Thr Ala Lys Val Ile Val Gly Asp Glu Lys Thr Met Met Val Asn Leu

```
                755                 760                 765
Ala Glu Gly Ala Thr Val Ile Gly Gly Ser Ala Asp Pro Val Asn Ala
        770                 775                 780

Arg Lys Val Phe Asp Gly Gln Leu Gly Ser Glu Thr Asp Asn Ile Ser
785                 790                 795                 800

Leu Gly Trp Asp Ser Lys Gln Ser Ile Ile Phe Lys Leu Lys Glu Asp
                805                 810                 815

Gly Leu Ile Lys His Trp Arg Phe Phe Asn Asp Ser Ala Arg Asn Pro
            820                 825                 830

Glu Thr Thr Asn Lys Pro Ile Gln Glu Ala Ser Leu Gln Ile Phe Asn
        835                 840                 845

Ile Lys Asp Tyr Asn Leu Asp Asn Leu Leu Glu Asn Pro Asn Lys Phe
    850                 855                 860

Asp Asp Glu Lys Tyr Trp Ile Thr Val Asp Thr Tyr Ser Ala Gln Gly
865                 870                 875                 880

Glu Arg Ala Thr Ala Phe Ser Asn Thr Leu Asn Asn Ile Thr Ser Lys
                885                 890                 895

Tyr Trp Arg Val Val Phe Asp Thr Lys Gly Asp Arg Tyr Ser Ser Pro
            900                 905                 910

Val Val Pro Glu Leu Gln Ile Leu Gly Tyr Pro Leu Pro Asn Ala Asp
        915                 920                 925

Thr Ile Met Lys Thr Val Thr Thr Ala Lys Glu Leu Ser Gln Gln Lys
    930                 935                 940

Asp Lys Phe Ser Gln Lys Met Leu Asp Glu Leu Lys Ile Lys Glu Met
945                 950                 955                 960

Ala Leu Glu Thr Ser Leu Asn Ser Lys Ile Phe Asp Val Thr Ala Ile
                965                 970                 975

Asn Ala Asn Ala Gly Val Leu Lys Asp Cys Ile Glu Lys Arg Gln Leu
            980                 985                 990

Leu Lys Lys
    995
```

<210> SEQ ID NO 6
<211> LENGTH: 995
<212> TYPE: PRT
<213> ORGANISM: Artificial Sequence
<220> FEATURE:
<223> OTHER INFORMATION: Synthetic Construct

<400> SEQUENCE: 6

```
Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Val Gln Lys Gly Leu Pro
        35                  40                  45

Ser Ile Asp Ser Leu His Tyr Leu Ser Glu Asn Ser Lys Glu Phe
    50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
            100                 105                 110

Leu Tyr Gly Gly Tyr Phe Arg Thr Trp His Asp Lys Thr Ser Asp Pro
```

-continued

```
            115                 120                 125
Thr Glu Lys Asp Lys Val Asn Ser Met Gly Glu Leu Pro Lys Glu Val
130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
            180                 185                 190

Asn Ser Gly Ile Ala Glu Asp Thr Ser Lys Tyr Pro Asn Thr Pro Glu
        195                 200                 205

Gly Asn Lys Ala Leu Ala Lys Ala Ile Val Asp Glu Tyr Val Tyr Lys
    210                 215                 220

Tyr Asn Leu Asp Gly Leu Asp Val Glu Val His Asp Ser Ile Pro
225                 230                 235                 240

Lys Val Asp Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
            260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Gln Val
    290                 295                 300

Tyr Gly Ser Gln Gly Glu Lys Gly Gly Trp Glu Pro Val Ser Asn Arg
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Tyr Glu Glu Asn Ala
            340                 345                 350

Gln Glu Gly Asn Leu Trp Tyr Asp Ile Asn Ser Arg Lys Asp Glu Asp
        355                 360                 365

Lys Ala Asn Gly Ile Asn Thr Asp Ile Thr Gly Thr Arg Ala Glu Arg
    370                 375                 380

Tyr Ala Arg Trp Gln Pro Lys Thr Gly Gly Val Lys Gly Gly Ile Phe
385                 390                 395                 400

Ser Tyr Ala Ile Asp Arg Asp Gly Val Ala His Gln Pro Lys Lys Tyr
                405                 410                 415

Ala Lys Gln Lys Glu Phe Lys Asp Ala Thr Asp Asn Ile Phe His Ser
            420                 425                 430

Asp Tyr Ser Val Ser Lys Ala Leu Lys Thr Val Met Leu Lys Asp Lys
        435                 440                 445

Ser Tyr Asp Leu Ile Asp Glu Lys Asp Phe Pro Asp Lys Ala Leu Arg
    450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
            500                 505                 510

Ser Arg Ile Thr Lys Leu Asp Arg Ser Val Leu Pro Ala Asn Met Lys
        515                 520                 525

Pro Gly Lys Asp Thr Leu Glu Thr Val Leu Glu Thr Tyr Lys Lys Asp
    530                 535                 540
```

-continued

```
Asn Lys Glu Glu Pro Ala Thr Ile Pro Pro Val Ser Leu Lys Val Ser
545                 550                 555                 560
Gly Leu Thr Gly Leu Lys Glu Leu Asp Leu Ser Gly Phe Asp Arg Glu
            565                 570                 575
Thr Leu Ala Gly Leu Asp Ala Ala Thr Leu Thr Ser Leu Glu Lys Val
            580                 585                 590
Asp Ile Ser Gly Asn Lys Leu Asp Leu Ala Pro Gly Thr Glu Asn Arg
            595                 600                 605
Gln Ile Phe Asp Thr Met Leu Ser Thr Ile Ser Asn His Val Gly Ser
            610                 615                 620
Asn Glu Gln Thr Val Lys Phe Asp Lys Gln Lys Pro Thr Gly His Tyr
625                 630                 635                 640
Pro Asp Thr Tyr Gly Lys Thr Ser Leu Arg Leu Pro Val Ala Asn Glu
            645                 650                 655
Lys Val Asp Leu Gln Ser Gln Leu Leu Phe Gly Thr Val Thr Asn Gln
            660                 665                 670
Gly Thr Leu Ile Asn Ser Glu Ala Asp Tyr Lys Ala Tyr Gln Asn His
            675                 680                 685
Lys Ile Ala Gly Arg Ser Phe Val Asp Ser Asn Tyr His Tyr Asn Asn
690                 695                 700
Phe Lys Val Ser Tyr Glu Asn Tyr Thr Val Lys Val Thr Asp Ser Thr
705                 710                 715                 720
Leu Gly Thr Thr Thr Asp Lys Thr Leu Ala Thr Asp Lys Glu Glu Thr
            725                 730                 735
Tyr Lys Val Asp Phe Phe Ser Pro Ala Asp Lys Thr Lys Ala Val His
            740                 745                 750
Thr Ala Lys Val Ile Val Gly Asp Glu Lys Thr Met Met Val Asn Leu
            755                 760                 765
Ala Glu Gly Ala Thr Val Ile Gly Gly Ser Ala Asp Pro Val Asn Ala
770                 775                 780
Arg Lys Val Phe Asp Gly Gln Leu Gly Ser Glu Thr Asp Asn Ile Ser
785                 790                 795                 800
Leu Gly Trp Asp Ser Lys Gln Ser Ile Ile Phe Lys Leu Lys Glu Asp
            805                 810                 815
Gly Leu Ile Lys His Trp Arg Phe Phe Asn Asp Ser Ala Arg Asn Pro
            820                 825                 830
Glu Thr Thr Asn Lys Pro Ile Gln Glu Ala Ser Leu Gln Ile Phe Asn
            835                 840                 845
Ile Lys Asp Tyr Asn Leu Asp Asn Leu Leu Glu Asn Pro Asn Lys Phe
            850                 855                 860
Asp Asp Glu Lys Tyr Trp Ile Thr Val Asp Thr Tyr Ser Ala Gln Gly
865                 870                 875                 880
Glu Arg Ala Thr Ala Phe Ser Asn Thr Leu Asn Asn Ile Thr Ser Lys
            885                 890                 895
Tyr Trp Arg Val Val Phe Asp Thr Lys Gly Asp Arg Tyr Ser Ser Pro
            900                 905                 910
Val Val Pro Glu Leu Gln Ile Leu Gly Tyr Pro Leu Pro Asn Ala Asp
            915                 920                 925
Thr Ile Met Lys Thr Val Thr Thr Ala Lys Glu Leu Ser Gln Gln Lys
            930                 935                 940
Asp Lys Phe Ser Gln Lys Met Leu Asp Glu Leu Lys Ile Lys Glu Met
945                 950                 955                 960
```

```
Ala Leu Glu Thr Ser Leu Asn Ser Lys Ile Phe Asp Val Thr Ala Ile
                965                 970                 975

Asn Ala Asn Ala Gly Val Leu Lys Asp Cys Ile Glu Lys Arg Gln Leu
            980                 985                 990

Leu Lys Lys
        995

<210> SEQ ID NO 7
<211> LENGTH: 995
<212> TYPE: PRT
<213> ORGANISM: Artificial Sequence
<220> FEATURE:
<223> OTHER INFORMATION: Synthetic Construct

<400> SEQUENCE: 7

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Val Gln Lys Gly Leu Pro
            35                  40                  45

Ser Ile Asp Ser Leu His Tyr Leu Ser Glu Asn Ser Lys Lys Glu Phe
    50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
            100                 105                 110

Leu Tyr Gly Gly Tyr Phe Arg Thr Trp His Asp Lys Thr Ser Asp Pro
        115                 120                 125

Thr Glu Lys Asp Lys Val Asn Ser Met Gly Glu Leu Pro Lys Glu Val
    130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
            180                 185                 190

Asn Ser Gly Ile Ala Glu Asp Thr Ser Lys Tyr Pro Asn Thr Pro Glu
        195                 200                 205

Gly Asn Lys Ala Leu Ala Lys Ala Ile Val Asp Glu Tyr Val Tyr Lys
    210                 215                 220

Tyr Asn Leu Asp Gly Leu Asp Val Gly Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
            260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Gln Val
    290                 295                 300

Tyr Gly Ser Gln Gly Glu Lys Gly Gly Trp Glu Pro Val Ser Asn Arg
305                 310                 315                 320
```

```
Pro Glu Lys Thr Met Glu Arg Trp Gln Gly Tyr Ser Lys Tyr Ile
            325                 330                 335

Arg Pro Glu Gln Tyr Met Ile Gly Phe Ser Phe Tyr Glu Glu Asn Ala
        340                 345                 350

Gln Glu Gly Asn Leu Trp Tyr Asp Ile Asn Ser Arg Lys Asp Glu Asp
            355                 360                 365

Lys Ala Asn Gly Ile Asn Thr Asp Ile Gly Thr Arg Ala Glu Arg
370                 375                 380

Tyr Ala Arg Trp Gln Pro Lys Thr Gly Val Lys Gly Gly Ile Phe
385                 390                 395                 400

Ser Tyr Ala Ile Asp Arg Asp Gly Val Ala His Gln Pro Lys Lys Tyr
            405                 410                 415

Ala Lys Gln Lys Glu Phe Lys Asp Ala Thr Asp Asn Ile Phe His Ser
        420                 425                 430

Asp Tyr Ser Val Ser Lys Ala Leu Lys Thr Val Met Leu Lys Asp Lys
            435                 440                 445

Ser Tyr Asp Leu Ile Asp Glu Lys Asp Phe Pro Asp Lys Ala Leu Arg
    450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
            485                 490                 495

Gly Leu Asn Lys Phe Lys Lys Leu Ala Gln Leu Asp Leu Ile Gly Leu
        500                 505                 510

Ser Arg Ile Thr Lys Leu Asp Arg Ser Val Leu Pro Ala Asn Met Lys
    515                 520                 525

Pro Gly Lys Asp Thr Leu Glu Thr Val Leu Glu Thr Tyr Lys Lys Asp
    530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
            565                 570                 575

Thr Leu Ala Gly Leu Asp Ala Ala Thr Leu Thr Ser Leu Glu Lys Val
            580                 585                 590

Asp Ile Ser Gly Asn Lys Leu Asp Leu Ala Pro Gly Thr Glu Asn Arg
    595                 600                 605

Gln Ile Phe Asp Thr Met Leu Ser Thr Ile Ser Asn His Val Gly Ser
    610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
            645                 650                 655

Lys Val Asp Leu Gln Ser Gln Leu Leu Phe Gly Thr Val Thr Asn Gln
        660                 665                 670

Gly Thr Leu Ile Asn Ser Glu Ala Asp Tyr Lys Ala Tyr Gln Asn His
            675                 680                 685

Lys Ile Ala Gly Arg Ser Phe Val Asp Ser Asn Tyr His Tyr Asn Asn
    690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
            725                 730                 735

Tyr Lys Val Asp Phe Phe Ser Pro Ala Asp Lys Thr Lys Ala Val His
```

```
                740                 745                 750
Thr Ala Lys Val Ile Val Gly Asp Glu Lys Thr Met Met Val Asn Leu
        755                 760                 765
Ala Glu Gly Ala Thr Val Ile Gly Gly Ser Ala Asp Pro Val Asn Ala
    770                 775                 780
Arg Lys Val Phe Asp Gly Gln Leu Gly Ser Glu Thr Asp Asn Ile Ser
785                 790                 795                 800
Leu Gly Trp Asp Ser Lys Gln Ser Ile Ile Phe Lys Leu Lys Glu Asp
                805                 810                 815
Gly Leu Ile Lys His Trp Arg Phe Phe Asn Asp Ser Ala Arg Asn Pro
            820                 825                 830
Glu Thr Thr Asn Lys Pro Ile Gln Glu Ala Ser Leu Gln Ile Phe Asn
        835                 840                 845
Ile Lys Asp Tyr Asn Leu Asp Asn Leu Leu Glu Asn Pro Asn Lys Phe
    850                 855                 860
Asp Asp Glu Lys Tyr Trp Ile Thr Val Asp Thr Tyr Ser Ala Gln Gly
865                 870                 875                 880
Glu Arg Ala Thr Ala Phe Ser Asn Thr Leu Asn Asn Ile Thr Ser Lys
                885                 890                 895
Tyr Trp Arg Val Val Phe Asp Thr Lys Gly Asp Arg Tyr Ser Ser Pro
            900                 905                 910
Val Val Pro Glu Leu Gln Ile Leu Gly Tyr Pro Leu Pro Asn Ala Asp
        915                 920                 925
Thr Ile Met Lys Thr Val Thr Thr Ala Lys Glu Leu Ser Gln Gln Lys
    930                 935                 940
Asp Lys Phe Ser Gln Lys Met Leu Asp Glu Leu Lys Ile Lys Glu Met
945                 950                 955                 960
Ala Leu Glu Thr Ser Leu Asn Ser Lys Ile Phe Asp Val Thr Ala Ile
                965                 970                 975
Asn Ala Asn Ala Gly Val Leu Lys Asp Cys Ile Glu Lys Arg Gln Leu
            980                 985                 990
Leu Lys Lys
        995

<210> SEQ ID NO 8
<211> LENGTH: 995
<212> TYPE: PRT
<213> ORGANISM: Artificial Sequence
<220> FEATURE:
<223> OTHER INFORMATION: Synthetic Construct

<400> SEQUENCE: 8

Met Asp Lys His Leu Leu Val Lys Arg Thr Leu Gly Cys Val Cys Ala
1               5                   10                  15
Ala Thr Leu Met Gly Ala Ala Leu Ala Thr His His Asp Ser Leu Asn
            20                  25                  30
Thr Val Lys Ala Glu Glu Lys Thr Val Gln Val Gln Lys Gly Leu Pro
        35                  40                  45
Ser Ile Asp Ser Leu His Tyr Leu Ser Glu Asn Ser Lys Lys Glu Phe
    50                  55                  60
Lys Glu Glu Leu Ser Lys Ala Gly Gln Glu Ser Gln Lys Val Lys Glu
65                  70                  75                  80
Ile Leu Ala Lys Ala Gln Gln Ala Asp Lys Gln Ala Gln Glu Leu Ala
                85                  90                  95
Lys Met Lys Ile Pro Glu Lys Ile Pro Met Lys Pro Leu His Gly Pro
```

```
                100                 105                  110
Leu Tyr Gly Gly Tyr Phe Arg Thr Trp His Asp Lys Thr Ser Asp Pro
            115                 120                 125
Thr Glu Lys Asp Lys Val Asn Ser Met Gly Glu Leu Pro Lys Glu Val
130                 135                 140
Asp Leu Ala Phe Ile Phe His Asp Trp Thr Lys Asp Tyr Ser Leu Phe
145                 150                 155                 160
Trp Lys Glu Leu Ala Thr Lys His Val Pro Lys Leu Asn Lys Gln Gly
            165                 170                 175
Thr Arg Val Ile Arg Thr Ile Pro Trp Arg Phe Leu Ala Gly Gly Asp
            180                 185                 190
Asn Ser Gly Ile Ala Glu Asp Thr Ser Lys Tyr Pro Asn Thr Pro Glu
            195                 200                 205
Gly Asn Lys Ala Leu Ala Lys Ala Ile Val Asp Glu Tyr Val Tyr Lys
            210                 215                 220
Tyr Asn Leu Asp Gly Leu Asp Val Asn Val Glu His Asp Ser Ile Pro
225                 230                 235                 240
Lys Val Asp Lys Lys Glu Asp Thr Ala Gly Val Glu Arg Ser Ile Gln
            245                 250                 255
Val Phe Glu Glu Ile Gly Lys Leu Ile Gly Pro Lys Gly Val Asp Lys
            260                 265                 270
Ser Arg Leu Phe Ile Met Asp Ser Thr Tyr Met Ala Asp Lys Asn Pro
            275                 280                 285
Leu Ile Glu Arg Gly Ala Pro Tyr Ile Asn Leu Leu Leu Val Gln Val
            290                 295                 300
Tyr Gly Ser Gln Gly Glu Lys Gly Gly Trp Glu Pro Val Ser Asn Arg
305                 310                 315                 320
Pro Glu Lys Thr Met Glu Glu Arg Trp Gln Gly Tyr Ser Lys Tyr Ile
            325                 330                 335
Arg Pro Glu Gln Tyr Met Ile Gly Phe Ser Phe Tyr Glu Glu Asn Ala
            340                 345                 350
Gln Glu Gly Asn Leu Trp Tyr Asp Ile Asn Ser Arg Lys Asp Glu Asp
            355                 360                 365
Lys Ala Asn Gly Ile Asn Thr Asp Ile Thr Gly Thr Arg Ala Glu Arg
            370                 375                 380
Tyr Ala Arg Trp Gln Pro Lys Thr Gly Gly Val Lys Gly Gly Ile Phe
385                 390                 395                 400
Ser Tyr Ala Ile Asp Arg Asp Gly Val Ala His Gln Pro Lys Lys Tyr
            405                 410                 415
Ala Lys Gln Lys Glu Phe Lys Asp Ala Thr Asp Asn Ile Phe His Ser
            420                 425                 430
Asp Tyr Ser Val Ser Lys Ala Leu Lys Thr Val Met Leu Lys Asp Lys
            435                 440                 445
Ser Tyr Asp Leu Ile Asp Glu Lys Asp Phe Pro Asp Lys Ala Leu Arg
            450                 455                 460
Glu Ala Val Met Ala Gln Val Gly Thr Arg Lys Gly Asp Leu Glu Arg
465                 470                 475                 480
Phe Asn Gly Thr Leu Arg Leu Asp Asn Pro Ala Ile Gln Ser Leu Glu
            485                 490                 495
Gly Leu Asn Lys Phe Lys Lys Leu Ala Gln Leu Asp Leu Ile Gly Leu
            500                 505                 510
Ser Arg Ile Thr Lys Leu Asp Arg Ser Val Leu Pro Ala Asn Met Lys
            515                 520                 525
```

```
Pro Gly Lys Asp Thr Leu Glu Thr Val Leu Glu Thr Tyr Lys Lys Asp
    530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
                565                 570                 575

Thr Leu Ala Gly Leu Asp Ala Ala Thr Leu Thr Ser Leu Glu Lys Val
            580                 585                 590

Asp Ile Ser Gly Asn Lys Leu Asp Leu Ala Pro Gly Thr Glu Asn Arg
        595                 600                 605

Gln Ile Phe Asp Thr Met Leu Ser Thr Ile Ser Asn His Val Gly Ser
    610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
                645                 650                 655

Lys Val Asp Leu Gln Ser Gln Leu Leu Phe Gly Thr Val Thr Asn Gln
            660                 665                 670

Gly Thr Leu Ile Asn Ser Glu Ala Asp Tyr Lys Ala Tyr Gln Asn His
        675                 680                 685

Lys Ile Ala Gly Arg Ser Phe Val Asp Ser Asn Tyr His Tyr Asn Asn
    690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
                725                 730                 735

Tyr Lys Val Asp Phe Phe Ser Pro Ala Asp Lys Thr Lys Ala Val His
            740                 745                 750

Thr Ala Lys Val Ile Val Gly Asp Glu Lys Thr Met Met Val Asn Leu
        755                 760                 765

Ala Glu Gly Ala Thr Val Ile Gly Gly Ser Ala Asp Pro Val Asn Ala
    770                 775                 780

Arg Lys Val Phe Asp Gly Gln Leu Gly Ser Glu Thr Asp Asn Ile Ser
785                 790                 795                 800

Leu Gly Trp Asp Ser Lys Gln Ser Ile Ile Phe Lys Leu Lys Glu Asp
                805                 810                 815

Gly Leu Ile Lys His Trp Arg Phe Phe Asn Asp Ser Ala Arg Asn Pro
            820                 825                 830

Glu Thr Thr Asn Lys Pro Ile Gln Glu Ala Ser Leu Gln Ile Phe Asn
        835                 840                 845

Ile Lys Asp Tyr Asn Leu Asp Asn Leu Leu Glu Asn Pro Asn Lys Phe
    850                 855                 860

Asp Asp Glu Lys Tyr Trp Ile Thr Val Asp Thr Tyr Ser Ala Gln Gly
865                 870                 875                 880

Glu Arg Ala Thr Ala Phe Ser Asn Thr Leu Asn Asn Ile Thr Ser Lys
                885                 890                 895

Tyr Trp Arg Val Val Phe Asp Thr Lys Gly Asp Arg Tyr Ser Ser Pro
            900                 905                 910

Val Val Pro Glu Leu Gln Ile Leu Gly Tyr Pro Leu Pro Asn Ala Asp
        915                 920                 925

Thr Ile Met Lys Thr Val Thr Thr Ala Lys Glu Leu Ser Gln Gln Lys
    930                 935                 940
```

-continued

Asp Lys Phe Ser Gln Lys Met Leu Asp Glu Leu Lys Ile Lys Glu Met
945                 950                 955                 960

Ala Leu Glu Thr Ser Leu Asn Ser Lys Ile Phe Asp Val Thr Ala Ile
                965                 970                 975

Asn Ala Asn Ala Gly Val Leu Lys Asp Cys Ile Glu Lys Arg Gln Leu
            980                 985                 990

Leu Lys Lys
        995

<210> SEQ ID NO 9
<211> LENGTH: 52
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (19)..(21)
<223> OTHER INFORMATION: n is a, c, g, or t

<400> SEQUENCE: 9
cgtaaattcg tgctcaatnn naatatctag tccatcgaca ccacgatcag tt    52

<210> SEQ ID NO 10
<211> LENGTH: 52
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (32)..(34)
<223> OTHER INFORMATION: n is a, c, g, or t

<400> SEQUENCE: 10
aactgatcgt ggtgtcgatg gactagatat tnnnattgag cacgaattta cg    52

<210> SEQ ID NO 11
<211> LENGTH: 843
<212> TYPE: PRT
<213> ORGANISM: Streptococcus pyogenes serotype M49

<400> SEQUENCE: 11

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Thr Gly Lys Thr Asp Gln
            35                  40                  45

Gln Val Gly Ala Lys Leu Val Gln Glu Ile Arg Glu Gly Lys Arg Gly
        50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln Thr Ile Gly Val Asn Glu Leu
    130                 135                 140

```
Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Asp Ile Glu His Glu Phe Thr Asn Lys
                180                 185                 190

Arg Thr Pro Glu Glu Asp Ala Arg Ala Leu Asn Val Phe Lys Glu Ile
                195                 200                 205

Ala Gln Leu Ile Gly Lys Asn Gly Ser Asp Lys Ser Lys Leu Leu Ile
                210                 215                 220

Met Asp Thr Thr Leu Ser Val Glu Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
                260                 265                 270

Asn Tyr Ile Asp Ala Ser Gln Phe Met Ile Gly Phe Ser Phe Phe Glu
                275                 280                 285

Glu Ser Ala Ser Lys Gly Asn Leu Trp Phe Asp Val Asn Glu Tyr Asp
290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr
                340                 345                 350

Tyr Lys Asn Arg Thr Ser Thr Asn Leu Gln Arg His Glu Val Asp Asn
                355                 360                 365

Ile Ser His Thr Asp Tyr Thr Val Ser Arg Lys Leu Lys Thr Leu Met
                370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
                405                 410                 415

Asp Leu Glu Arg Tyr Asn Lys Thr Leu Val Leu Thr Gly Asp Lys Ile
                420                 425                 430

Gln Asn Leu Lys Gly Leu Glu Lys Leu Ser Lys Leu Gln Lys Leu Glu
                435                 440                 445

Leu Arg Gln Leu Ser Asn Val Lys Glu Ile Thr Pro Glu Leu Leu Pro
                450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
                500                 505                 510

Asn Ser Leu Asp Leu Ser Glu Lys Ser Glu Asp Arg Lys Leu Leu Met
                515                 520                 525

Thr Leu Met Glu Gln Val Ser Asn His Gln Lys Ile Thr Val Lys Asn
                530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
```

-continued

```
                565                 570                 575
Leu Thr Asp Phe Val Phe Gly Thr Val Thr Lys Arg Asn Thr Phe Ile
            580                 585                 590

Gly Asp Glu Glu Ala Phe Ala Ile Tyr Lys Glu Gly Ala Val Asp Gly
        595                 600                 605

Arg Gln Tyr Val Ser Lys Asp Tyr Thr Tyr Glu Ala Phe Arg Lys Asp
    610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
            645                 650                 655

Val Ser Asp Gly Glu Lys Val Val His His Met Lys Leu Asn Ile Gly
            660                 665                 670

Ser Gly Ala Ile Met Met Glu Asn Leu Ala Lys Gly Ala Lys Val Ile
        675                 680                 685

Gly Thr Ser Gly Asp Phe Glu Gln Ala Lys Lys Ile Phe Asp Gly Glu
    690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
            725                 730                 735

Glu Thr Asn Thr Glu Ile Lys Thr Asp Ser Ser Leu Asn Val Ala Lys
            740                 745                 750

Gly Arg Leu Gln Ile Leu Lys Asp Thr Thr Ile Asp Leu Glu Lys Met
        755                 760                 765

Asp Ile Lys Asn Arg Lys Glu Tyr Leu Ser Asn Asp Glu Asn Trp Thr
    770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
            805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Lys Asp
            835                 840
```

GENERATION AND COMPARATIVE KINETIC ANALYSIS OF NEW GLYCOSYNTHASE MUTANTS FROM *STREPTOCOCCUS PYOGENES* ENDOGLYCOSIDASES FOR ANTIBODY GLYCOENGINEERING

CROSS-REFERENCE TO RELATED APPLICATION

This application claims priority to U.S. Provisional Application No. 62/526,635 filed on Jun. 29, 2017, the contents of which are incorporated by reference herein for all purposes.

GOVERNMENT RIGHTS IN INVENTION

This invention was made with government support under R01GM096973B and R01 GM080374 by the US National Institutes of Health. The government has certain rights in the invention.

BACKGROUND OF THE INVENTION

Field of the Invention

The invention relates to glycoprotein synthesis, and more particularly, to the use of a recombinant and mutant Endo S, an Endo-β-N-acetylglucosaminidase from *Streptococcus pyogenes*, that possesses transglycosylation activity and limited hydrolyzing activity thereby providing for efficient glycosylation remodeling of antibody-Fc domain.

Description of the Related Art

Therapeutic monoclonal antibodies (mAbs) represent a rapidly expanding class of biologics that are widely used for the treatment of cancer, inflammation, and infectious diseases[1-3]. Previous studies have shown that glycosylation affects a wide range of properties of antibodies, including structural integrity, serum half-life, effector functions and therapeutic efficacy[4]. For instance, a lack of core fucosylation on IgG Fc N-glycans at Asn-297 can significantly enhance antibody-dependent cellular cytotoxicity (ADCC), and the engineered antibody therapeutics with low fucose content showed substantially enhanced therapeutic efficacy over their fucosylated counterparts[5-7]. Moreover, a minor sialylated component of intravenous immunoglobulin (IVIG) has demonstrated anti-inflammatory effects in animal models[8-10]. Nevertheless, antibody preparations from natural resources or recombinant protein expression typically contain a heterogeneous mixture of glycan structures and are not usually optimized for structure-function studies or their therapeutic purposes[11, 12]. For example, only a small percentage of antibody therapeutics carries non-fucosylated N-glycoforms that are most effective for their functions as anti-cancer drugs[13, 14]. Monoclonal antibodies carrying homogeneous glycan structures become essential materials for studying antibody glycosylation and the therapeutic outcome of antibody-based drugs.

Tremendous efforts have been pursued to optimize antibody glycosylation through engineering of the glycosylation biosynthetic pathway in various host expression systems[15-17]. Nevertheless, complete control of the glycosylation profile by host expression engineering remains a challenge and the glycoforms that can be accessed this way are limited[15-17]. An alternative approach to circumvent the heterogeneity of antibody glycosylation is to perform in vitro chemoenzymatic glycan remodeling using an endoglycosidase-catalyzed deglycosylation and glycosynthase-catalyzed re-glycosylation protocol[18-21]. In this method, heterogeneous N-glycans of antibody are released by the wild-type endoglycosidase, leaving only the innermost GlcNAc or Fucα1,6G1cNAc residue intact on the antibody backbone. Then, the well-defined glycan structures can be re-attached to the GlcNAc- or Fucα,1,6G1cNAc containing antibody by an endoglycosidase or an endo-glycosynthase mutant in a site-specific manner to produce antibody with homogeneous glycoforms. In 2012, two endo-glycosynthase mutants, D233A and D233Q, of an endoglycosidase from *Streptococcus pyogenes* (Endo-S) were created that were able to transfer complex type N-glycans to the deglycosylated rituximab, which represents the first endo-glycosynthases generated from the GH family 18 enzymes[20]. This discovery has since opened a new avenue to access structurally well-defined antibody glycoforms for structural and functional studies[22-26]. The crystal structure of Endo-S has been also solved and provided some insight into its catalytic mechanism[27, 28]. More recently new endo-glycosynthases mutants with much broader substrate specificity were also generated from Endo-S2[29], an endoglycosidase from *Streptococcus pyogenes* serotype M49 (Endo-S2)[30]. A recent study of a systematic mutagenesis on Endo-S2 has shown that the nature of the amino acid substituents at the critical Asp-184 residue has a significant impact on the transglycosylation and/or the residual hydrolysis activity[29]. However, a systematic mutagenesis on prototype enzyme Endo-S at the critical Asp-233 site has not been reported and the mechanism behind the observed difference in catalysis by different mutants remains to be characterized.

In light of the above known activities of Endo S, it would be advantageous to provide a mutant Endo-S that exhibits transglycosylating activity with reduced hydrolyzing activity.

SUMMARY OF THE INVENTION

The present invention provides for recombinant Endo-S and selected mutants thereof that exhibit reduced hydrolysis activity and increased transglycosylation activity for the synthesis of IgG antibodies and Fc fragments thereof, wherein a desired sugar chain is added to a core fucosylated or nonfucosylated GlcNAc-IgG acceptor. As such, the present invention allows for the synthesis and remodeling of therapeutic antibodies and Fc fragments thereof to provide for certain biological activities, such as, prolonged half-life time in vivo, less immunogenicity, enhanced in vivo activity, increased targeting ability, and/or ability to deliver a therapeutic agent.

In one aspect, the present invention provides for transglycosylation activity of an endo-β-N-acetylglucosamindase of *Streptococcus pyogenes* (SEQ ID NO: 1) and mutants thereof, wherein the mutants have at least 95% homology thereto and exhibit transglycosylation activity on both core fucosylated and nonfucosylated GlcNAc-IgG acceptors, wherein the endoglycosidases enable the transfer of an oligosaccharide (in the form of an activated sugar oxazoline) en bloc to a fucosylated or nonfucosylated GlcNAc-IgG (or an Fc fragment thereof) to form a new glycoform of IgG (or an Fc fragment thereof).

In another aspect, the present invention provides for Endo-S mutants that show remarkably enhanced transglycosylation efficiency and diminished or abrogated product hydrolytic activity. Mutants preferably include site-specific mutations including a mutation at Asp-233 including in particular, D233C (SEQ ID NO: 5), D233E (SEQ ID NO: 6), D233G (SEQ ID NO: 7), D233M (SEQ ID NO: 2) and D233N (SEQ ID NO: 8) and mutants have at least 95% homology thereto that demonstrate transglycosylation activities. A preferred mutant is D233M (SEQ ID NO: 2) but not limited thereto.

In a further aspect, the present invention provides for a chemoenzymatic method for the preparation of a homogeneous core fucosylated or nonfucosylated glycoforms of IgG antibodies, comprising:
a. providing an acceptor selected from the group consisting of a core fucosylated GlcNAc-IgG, nonfucosylated GlcNAc-IgG or corresponding IgG-Fc fragments; and
b. reacting the acceptor with a donor substrate including an activated oligosaccharide moiety, in the presence of *Streptococcus pyogenes* Endo-S Asp-233-Met mutant to transfer the activated oligosaccharide moiety to the acceptor and yield the homogeneous fucosylated or nonfucosylated glycoprotein.

In a still further aspect, the present invention provides a method for preparing a core-fucosylated IgG or IgG-Fc fragment having a predetermined oligosaccharide moiety, comprising:
a. providing a core-fucosylated IgG acceptor comprising an asparagine-linked core-fucosylated N-acetylglucosamine (GlcNAc) residue; and
b. enzymatically reacting the core-fucosylated IgG acceptor with an activated oligosaccharide donor in the presence of Endoglycosidase-S D233M (SEQ ID NO: 2) mutant or mutants have at least 95% homology thereto, wherein the activated oligosaccharide donor carries an oligosaccharide moiety comprising a predetermined number and type of sugar residues, wherein the oligosaccharide moiety is covalently linked to the core-fucosylated IgG acceptor, thereby preparing the core-fucosylated IgG or IgG-Fc fragment having the predetermined oligosaccharide moiety.

In yet another aspect, the present invention provides for an activated oligosaccharide moiety, such as glycan or oligosaccharide oxazoline, glycosyl fluoride, glycosyl azide or an aryl glycoside, as a donor substrate for the synthesis of homogeneous core-fucosylated glycoproteins or nonfucosylated glycoproteins. Preferably the activated oligosaccharide moiety is an oligosaccharide oxazoline.

In a further aspect, the present invention relates to a chemoenzymatic method for the preparation of a homogeneous fucosylated or nonfucosylated monomer antibody or Fc fragment thereof, said method comprising:
a. providing an acceptor selected from core fucosylated or nonfucosylated GlcNAc-antibody or Fc fragment thereof; and
b. reacting the acceptor with a donor substrate in the presence a *Streptococcus pyogenes* Endo-S Asp-233-Met mutant (SEQ ID NO: 2) or mutants have at least 95% homology thereto, wherein the donor substrate comprises a predetermined oligosaccharide component with a defined number and type of sugar residues and specific linkage types, thereby providing the homogeneous fucosylated or nonfucosylated monomer antibody or Fc fragment thereof. In one embodiment, a fucosylated GlcNAc containing protein is an alpha-1-6-fucosyl-GlcNAc-protein.

In another aspect, the present invention relates to a method of remodeling an antibody or Fc fragment thereof with an oligosaccharide having a predetermined oligosaccharide component with a defined number and type of sugar residues and with specific linkage types, the method comprising:
a. providing a core fucosylated antibody or Fc fragment thereof comprising Fc N-glycans;
b. treating the core fucosylated antibody or Fc fragment with a hydrolyzing endo-enzyme to yield a Asn-linked GlcNAc moiety; and
c. attaching the oligosaccharide to the Asn-linked GlcNAc moiety in the presence of an Endo-S mutant having an amino acid sequence consisting of SEQ ID NO: 2, thereby adding the predetermined oligosaccharide component.

In a further aspect, the present invention relates to a remodeling method of a core fucosylated or nonfucosylated IgG or IgG-Fc fragment with an oligosaccharide having a predetermined oligosaccharide component with a defined number and type of sugar residues and with specific linkage types, the method comprising:
providing a core fucosylated or nonfucosylated IgG or IgG-Fc fragment obtained from natural or recombinant sources carrying heterogeneous N-glycans;
treating the natural or recombinant IgG or IgG-Fc fragment with an endo-enzyme (a wild type endoglycosidase or a mutant endoglycosidase with efficient hydrolytic activity) to hydrolyze the bond between the two GlcNAc residues positioned closest to the peptide domain thereby forming a deglycosylated protein carrying a core fucosylated or nonfucosylated GlcNAc-acceptor; and
attaching the predetermined oligosaccharide component to the GlcNAc-acceptor to reconstitute the natural beta-1,4-glycosidic bond through transglycosylation with a *Streptococcus pyogenes* Endo-S Asp-233 mutant having an amino acid sequence SEQ ID NO: 2 or mutants have at least 95% homology thereto, thereby adding the predetermined the oligosaccharide component to remodel the core fucosylated or nonfucosylated IgG or IgG-Fc fragment.

Applicable oligosaccharide oxazolines include, but not limited to, high-mannose type, hybrid type, sialoglycan oxazoline and complex type N-glycan, as well as their selectively modified derivatives such as those with specific tags. Preferably, di-, tri-, tetra-, penta-, hexyl-, hepta-, octyl-, nona-, deca-, or undeca-saccharide oxazolines are utilized as donor substrates for a highly efficient chemoenzymatic synthesis of homogeneous core fucosylated or nonfucosylated IgG antibodies and IgG-Fc fragments.

In yet another aspect, the present invention relates to a method to synthesize a modified antibody or fragment thereof, the method comprising;
providing a naturally existing IgG antibody, a recombinant antibody or a Fc domain carrying Fc N-glycans as precursors;
Fc deglycosylating using an endoglycosidase such as a wild Endo-S to deglycosylate the Fc domain to form a GlcNAc-acceptor; wherein the GlcNAc-acceptor is positioned on the Fc region of the antibody and the GlcNAc-acceptor is either core fucosylated or nonfucosylated; and
transglycosylating the GlcNAc-acceptor in the naturally existing IgG antibody, the recombinant antibody or the Fc domain with an oligosaccharide oxazoline or a sialoglycan oxazoline having a predetermined number of sugar residues under the catalysis of an Endo-S mutant enzyme comprising SEQ ID NO: 2 or mutants have at least 95% homology thereto form the modified antibody with the predetermined number of sugar residues.

In yet another aspect, the present invention provides a method of remodeling an intravenous immunoglobulin (IVIG) exhibiting Fc-sialylated glycoforms, the method comprising:
a. providing an IVIG carrying Fc N-glycans;
b. Fc deglycosylating the Fc N-glycans using an endoglycosidase including wild Endo-S to form GlcNAc-acceptors; wherein the GlcNAc-acceptors are positioned on the Fc region of the IVIG and the GlcNAc-acceptors are either fucosylated or nonfucosylated; and
c. transglycosylating the GlcNAc-acceptors with a sialoglycan oxazoline having a predetermined number of sugar residues under the catalysis of a Endo-S mutant enzyme comprising SEQ ID NO: 2 or mutants have at least 95% homology thereto to form a sialylated WIG.

Another aspect of the present invention provides for an IVIG preparation containing composition comprising at least 90% of homogeneous sialylated Fc glycoforms to increase anti-inflammatory activity, wherein the sialylated Fc glycoforms are synthesized using a *Streptococcus pyogenes* Endo-S Asp-233-Met mutant (SEQ ID NO: 2) in combination with a GlcNAc moiety positioned on the Fc region of a deglycosylated IVIG and a sialoglycan oxazoline having a predetermined number of sugar residues.

In a still further aspect, the present invention relates to a method of synthesizing homogeneous core fucosylated or nonfucosylated IgG antibodies or IgG-Fc fragments, the method comprising:
a. providing a natural or recombinant IgG antibody or IgG-Fc fragment, wherein the recombinant IgG or IgG-Fc is produced from a typical protein expression system, including but not limited to yeast, insect, plant, and any mammalian expression system;
b. removing the N-glycans by an enzyme selected from the group consisting of Endo-H, Endo-A, Endo-S, and/or Endo-F3 to form a core fucosylated or nonfucosylated GlcNAc-containing protein;
c. providing a sugar oxazoline or sialoglycan oxazoline with a desired oligosaccharide component comprising a defined number and type of sugar residues in the chain; and
d. enzymatically transglycosylating the fucosylated or nonfucosylated GlcNAc-containing protein with a sugar oxazoline having a desired number of sugar residues or sialoglycan oxazoline having a desired number of sugar and sialic acid residues with an endoglycosidase selected from the group consisting of a *Streptococcus pyogenes* Endo-S Asp-233 mutant having a sequence SEQ ID NO: 2 or mutants have at least 95% homology thereto, thereby forming a homogeneous core fucosylated or nonfucosylated IgG antibody or IgG-Fc fragment having an extension of desired number of sugar residues and/or sialic acid.

It is envisioned that the oligosaccharide oxazoline or sialoglycan oxazoline having a predetermined oligosaccharide component with a defined number and type of sugar residues may further comprises an additional moiety or tag including, a therapeutic agent or drug such as for treating cancer, HIV or other viruses, substances that activates receptors on the cell plasma membrane, agents that affects intracellular chemistry, agents that affects cellular physics, genes, gene analogs, RNA, RNA analogs, DNA, DNA analogs, amino acid sequences of surface receptors such as CCR5 or CD4, antigenic structure having affinity for a specific antibody; amino acid sequences of receptor ligands such as gp120, gp41 or gp160, receptor antagonists, receptor blockers, enzymes, enzyme substrates, enzyme inhibitors, enzyme modulators, therapeutic proteins, protein analogs, metabolites, metabolite analogs, oligonucleotides, oligonucleotide analogs, antigens, antigen analogs, antibodies or fragments thereof, antibody analogs, an antibody different from the modified antibody which is reactive to another receptor bacteria, viruses, inorganic ions, metal ions, metal clusters, polymers, fluorescent compounds and any combinations thereof.

As such, the present invention further provides a delivery device for delivering a drug or therapeutic agent having biological activity to treat a condition, the delivery device comprising: a remodeled IgG or IgG-Fc fragment having a predetermined sugar chain or sialoglycan and a therapeutic agent or drug attached to the terminal sugar residue or sialic acid.

The present invention envisions modifying monoclonal antibodies related to HIV including, but not limited to 17b, 48d, A32, C11, 2G12, F240, IgG1b12, 19e, X5, TNX-355 and F91, all of which are commercially available.

Further antibodies related to cancer or other diseases may also be remodeled for individual fit to certain receptors thereby increasing biological activity, the monoclonal antibodies may include, but are not limited to, cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, 1-131 tositumomab, efalizumab, bevacizumab, panitumumab, pertuzumab, natalizumab, etanercept, IGN101 (Aphton), voloximab (Biogen Idec and PDL BioPharm), Anti-CD80 mAb (Biogen Idec), Anti-CD23 mAb (Biogen Idel), CAT-3888 (Cambridge Antibody Technology), CDP-791 (Imclone), erapotuzumab (Immunomedics), MDX-010 (Medarex and BMS), MDX-060 (Medarex), MDX-070 (Medarex), matuzumab (Merck), CP-675,206 (Pfizer), CAL (Roche), SGN-30 (Seattle Genetics), zanolimumab (Serono and Genmab), adecatumumab (Sereno), oregovomab (United Therapeutics), nimotuzumab (YM Bioscience), ABT-874 (Abbott Laboratories), denosumab (Amgen), AM 108 (Amgen), AMG 714 (Amgen), fontolizumab (Biogen Idec and PDL BioPharm), daclizumab (Biogent Idec and PDL BioPharm), golimumab (Centocor and Schering-Plough), CNTO 1275 (Centocor), ocrelizumab (Genetech and Roche), HuMax-CD20 (Genmab), belimumab (HGS and GSK), epratuzumab (Immunomedics), MLN1202 (Millennium Pharmaceuticals), visilizumab (PDL BioPharm), tocilizumab (Roche), ocrerlizumab (Roche), certolizumab pegol (UCB, formerly Celltech), eculizumab (Alexion Pharmaceuticals), pexelizumab (Alexion Pharmaceuticals and Procter & Gamble), abciximab (Centocor), ranibizimumab (Genetech), mepolizumab (GSK), TNX-355 (Tanox), or MYO-029 (Wyeth).

A still further aspect of the invention relates to a method of remodeling an antibody which initially includes a heterogeneous sugar chain, the method comprising:
a. removing the heterogeneous sugar chain from the antibody with an endoglycosidase to leave a single fucosylated- or nonfucosylated-GlcNAc moiety attached to an original glycosylation site; and
b. transferring a core oligosaccharide or sialoglycan oxazoline with at least one tag to the fucosylated- or -nonfucosylated GlcNAc moiety by an endoglycosidase catalyzed transglycosylation to yield a tagged antibody, wherein the endoglycosidase is selected from the group consisting of Endo-S mutant comprising SEQ ID NO: 2.

The tag moiety may include, but is not limited to, antigens, therapeutic drugs such as for cancer or HIV, toxins, fluorescent probes, biotin, PEG species, lipids, or nucleotides.

In another aspect, the present invention provides for a composition comprising a *Streptococcus pyogenes* Endo-S Asp-233 mutant (D233M) comprising amino acid sequence SEQ ID NO:2.

In yet another aspect, the present invention provides a substantially homogeneous preparation of core fucosylate or nonfucosylated antibody or Fc fragment thereof having a predetermined oligosaccharide moiety, wherein the substantially homogeneous preparation is produced by any of the aforementioned methods. Also provided are compositions comprising such homogeneous preparations.

In a still further aspect, the present invention provides for a method of treatment using a remodeled antibody having a desired glycosylation state and/or sialylated form in an amount sufficient to modulate biological activity in the treated subject.

Other aspects, features and embodiments of the invention will be more fully apparent from the ensuing disclosure and appended claims.

DETAILED DESCRIPTION OF THE INVENTION

Figure 1:
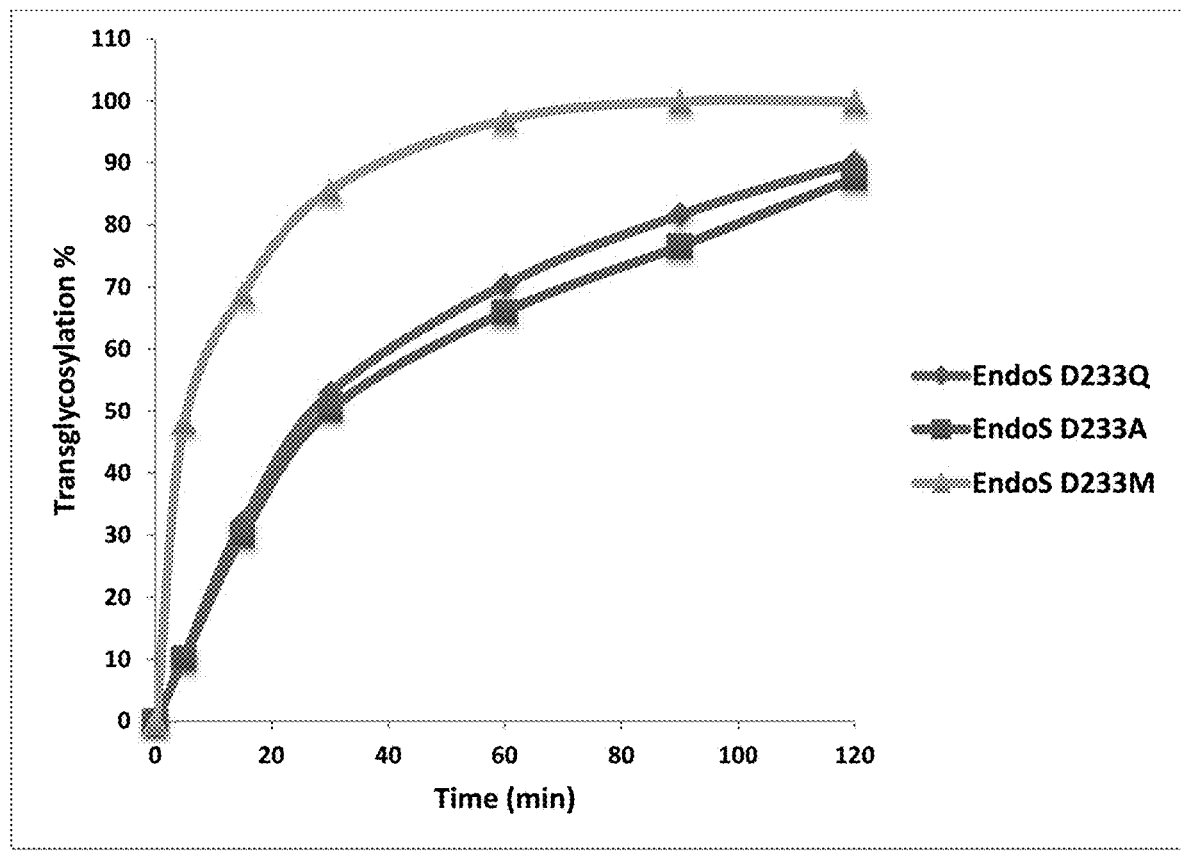
FIG. 1 shows a comparison of the transglycosylation efficiencies between Endo-S D233M (SEQ ID NO: 2) and the previously reported Endo-S D233Q (SEQ ID NO: 3) and Endo-S D233A (SEQ ID NO: 4) with SCT-Oxazoline. The data sets presented here are representative of three independent experiments.

The present invention shows a systematic mutagenic analysis at the Asp-233 of Endo-S and the evaluation of their catalytic activities. It was found herein that substitution of the Asp-233 with the other 19 conical amino acids led to significantly distinct effects on the hydrolysis and transglycosylation activity of Endo-S, with the D233M mutant showing the highest overall catalytic efficiency, defined by the transglycosylation/hydrolysis ratio. Kinetic studies on the D233M mutant of Endo-S, as well as the previously identified glycosynthase mutant D184M of wild type Endo-S2 (SEQ ID NO: 11), indicated that the enhanced overall catalytic efficacy of the Asp-to-Met mutants for the glycosyl donor substrate was mainly due to a much higher turnover number ($k_{cat}$) over the corresponding D233A or D184A mutant, respectively. Further, the Asp-to-Met mutants from both enzymes demonstrated a significantly higher substrate affinity for the glycosyl acceptor substrate, the deglycosylated antibody, than their Asp-to-Ala counterparts. These findings provide a mechanistic explanation for the enhanced catalytic activity of Endo-S D233M mutants The practice of the present invention will employ, unless otherwise indicated, conventional techniques of immunology, molecular biology, microbiology, cell biology and recombinant DNA, which are within the skill of the art. See, e.g., Sambrook, et al. MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

It is understood that aspects of the present invention described herein include "consisting" and/or "consisting essentially of" aspects.

Definitions

As used in the specification herein, "a" or "an" may mean one or more. As used herein in the claim(s), when used in conjunction with the word "comprising", the words "a" or "an" may mean one or more than one. As used herein "another" may mean at least a second or more.

As used herein, "biological activity" refers to pharmacodynamic and pharmacokinetic properties including, for example, molecular affinity or resultant biochemical or physiological effect, receptor affinity or resultant biochemical or physiological effect, non-receptor affinity or biochemical or physiological effect, efficacy, bioavailability, absorption, distribution, metabolism, or elimination.

As used herein, "sugar" refers to an oxidized or nonoxidized carbohydrate-containing molecule, including, but not limited to, a monosaccharide, disaccharide, trisaccharide, oligosaccharide, or polysaccharide, including, for example, N-acetylglucosamine, mannose, galactose, N-acetylneuraminic acid (sialic acid), glucose, fructose, fucose, sorbose, rhamnose, mannoheptulose, N-acetylgalactosamine, dihydroxyacetone, xylose, xylulose, arabinose, glyceraldehyde, sucrose, lactose, maltose, trehalose, cellobiose or any combination thereof of the L- or D-isomer. Sugar further refers to, such molecules produced naturally, recombinantly, synthetically, and/or semi-synthetically.

As used herein, "homogenous" refers to core fucosylated glycoproteins or nonfucosylated glycoproteins wherein the oligosaccharide component comprises at least 75%, more preferably at least 80%, at least 85% or at least 90%, and most preferably at least 95% of the same number and types of sugar residues.

As used herein, "protein" or "glycoprotein" is interchangeable with the terms peptide and glycopeptide.

As used herein, "homology" refers to amino acid sequence having substantial identity or similarity between two polypeptides and having at least 90%, and more preferably at least 95% similarity to a reference polypeptide. For polypeptides, the length of comparison to obtain the above-described percent homologies between sequences will generally be at least 25 amino acids, alternatively at least 50 amino acids, more likely at least 100 amino acids, and most likely 200 amino acids or more. Substantially identity or homologous polypeptides include additions, truncations, internal deletions or insertions, conservative and non-conservative substitutions, or other modifications located at positions of the amino acid sequence which do not destroy the function of the endoglycosidase. Those of skill in the art will recognize the numerous amino acids that can be modified or substituted with other chemically similar residues without substantially altering activity.

As used herein, "modulates" refers to an increase or decrease in "biological activity", as defined above, when comparing to a glycosylation-engineered antibody of the present invention to a non-glycosylation-engineered antibody.

As used herein, "immunoglobulin molecule" or "antibodies," refers to molecules that contain an antigen binding site which specifically binds an antigen or an Fc region that binds to cell receptors. Structurally, the simplest naturally occurring antibody (e.g., IgG) comprises four polypeptide chains, two heavy (H) chains and two light (L) chains inter-connected by disulfide bonds. The natural immunoglobulins represent a large family of molecules that include several types of molecules, such as IgD, IgG, IgA, IgM and IgE. The term also encompasses hybrid antibodies, or altered antibodies, and fragments thereof, including Fc fragment(s).

Antibodies can be fragmented using conventional techniques as described herein and the fragments screened for utility in the same manner as described for whole antibodies. A Fab fragment of an immunoglobulin molecule is a multimeric protein consisting of the portion of an immunoglobulin molecule containing the immunologically active portions of an immunoglobulin heavy chain and an immunoglobulin light chain covalently coupled together and capable of specifically combining with an antigen. Fab and Fc fragments can be prepared by proteolytic digestion of substantially intact immunoglobulin molecules with papain using methods that are well known in the art. However, a Fab or Fc fragment may also be prepared by expressing in a suitable host cell the desired portions of immunoglobulin heavy chain and immunoglobulin light chain using methods known in the art.

As used herein, with respect to antibodies, "substantially pure" means separated from those contaminants that accompany it in its natural state or those contaminants generated or used in the process of the obtaining the antibody. This term further includes the desired product having a single glycosylation state, whether or not this state includes glycosylation at a single site or multiple sites. Typically, the antibody is substantially pure when it constitutes at least 60%, by weight, of the antibody in the preparation. For example, the antibody in the preparation is at least about 75%, in certain embodiments at least about 80%, in certain embodiments at about 85%, in certain embodiments at least about 90%, in certain embodiments at least about 95%, and most preferably at least about 99%, by weight, of the desired antibody. A substantially pure antibody includes a naturally, recombinantly, or synthetically produced antibody.

As used herein, "therapeutically effective amount" refers to an amount that results in an improvement or remediation of the symptoms of the disease or condition.

Antigens useful for attachment as a tag to a modified core fucosylated or nonfucosylated glycoprotein of the present invention and more preferably an antibody or fragment thereof may be a foreign antigen, an endogenous antigen, fragments thereof, or variants having the same functional activity.

As used herein, "endogenous antigen" refers to a protein or part thereof that is naturally present in the recipient animal cell or tissue, such as a cellular protein, an immunoregulatory agent, or a therapeutic agent.

As used herein, "foreign antigen" refers to a protein or fragment thereof, which is foreign to the recipient animal cell or tissue including, but not limited to, a viral protein, a parasite protein, an immunoregulatory agent, or a therapeutic agent.

The foreign antigen may be a protein, an antigenic fragment or antigenic fragments thereof that originate from viral and parasitic pathogens.

Alternatively, the foreign antigen may be encoded by a synthetic gene and may be constructed using conventional recombinant DNA methods; the synthetic gene may express antigens or parts thereof that originate from viral and parasitic pathogens. These pathogens can be infectious in humans, domestic animals or wild animal hosts.

The foreign antigen can be any molecule that is expressed by any viral or parasitic pathogen prior to or during entry into, colonization of, or replication in their animal host.

The viral pathogens, from which the viral antigens are derived include, but are not limited to, Orthomyxoviruses, such as influenza virus (Taxonomy ID: 59771); Retroviruses, such as RSV, HTLV-1 (Taxonomy ID: 39015) and HTLV-II (Taxonomy ID: 11909); Herpes viruses, such as EBV (Taxonomy ID: 10295), CMV (Taxonomy ID: 10358) or herpes simplex virus (ATCC #: VR-1487); Lentiviruses, such as HIV-1 (Taxonomy ID: 12721) and HIV-2 Taxonomy ID: 11709); Rhabdoviruses, such as rabies; Picomoviruses, such as Poliovirus (Taxonomy ID: 12080); Poxviruses, such as vaccinia Taxonomy ID: 10245); Rotavirus Taxonomy ID: 10912); and Parvoviruses, such as adeno-associated virus 1 (Taxonomy ID: 85106).

Examples of viral antigens include, but are not limited to, the human immunodeficiency virus antigens Nef (National Institute of Allergy and Infectious Disease HIV Repository Cat. #183; GenBank accession # AF238278), Gag, Env (National Institute of Allergy and Infectious Disease HIV Repository Cat. #2433; GenBank accession # U39362), Tat (National Institute of Allergy and Infectious Disease HIV Repository Cat. #827; GenBank accession # M13137), Rev (National Institute of Allergy and Infectious Disease HIV Repository Cat. #2088; GenBank accession # L14572), Pol (National Institute of Allergy and Infectious Disease HIV Repository Cat. #238; GenBank accession # AJ237568) and T cell and B cell epitopes of gp120; the hepatitis B surface antigen (GenBank accession # AF043578); rotavirus antigens, such as VP4 (GenBank accession # AJ293721) and VP7 (GenBank accession # AY003871); influenza virus antigens, such as hemagglutinin (GenBank accession # AJ404627); nucleoprotein (GenBank accession # AJ289872); and herpes simplex virus antigens, such as thymidine kinase (GenBank accession # AB047378).

The bacterial pathogens, from which the bacterial antigens are derived, include but are not limited to, *Mycobacterium* spp., *Helicobacter pylori*, *Salmonella* spp., *Shigella* spp., *E. coli*, *Rickettsia* spp., *Listeria* spp., *Legionella pneumoniae*, *Pseudomonas* spp., *Vibrio* spp., and *Borellia burgdorferi*.

Examples of protective antigens of bacterial pathogens include the somatic antigens of enterotoxigenic *E. coli*, such as the CFA/I fimbrial antigen and the nontoxic B-subunit of the heat-labile toxin; pertactin of *Bordetella pertussis*, adenylate cyclase-hemolysin of *B. pertussis*, fragment C of tetanus toxin of *Clostridium tetani*, OspA of Borellia *burgdorferi*, protective paracrystalline-surface-layer proteins of *Rickettsia prowazekii* and *Rickettsia typhi*, the listeriolysin (also known as "Llo" and "Hly") and/or the superoxide dismutase (also know as "SOD" and "p60") of *Listeria monocytogenes*; the urease of *Helicobacter pylori*, and the receptor-binding domain of lethal toxin and/or the protective antigen of *Bacillus* anthrax.

Example of antigens from biological weapons or pathogens include, but are not limited to, smallpox, anthrax, tularemia, plague, listeria, brucellosis, hepatitis, vaccinia, mycobacteria, coxsackievirus, tuberculosis, malaria, erhlichosis and bacterial meningitis.

The parasitic pathogens, from which the parasitic antigens are derived, include but are not limited to, *Plasmodium* spp., such as *Plasmodium falciparum* (ATCC #: 30145); Trypanosome spp., such as *Trypanosoma cruzi* (ATCC #: 50797); *Giardia* spp., such as *Giardia* intestinalis (ATCC #: 30888D); *Boophilus* spp.; *Babesia* spp., such as *Babesia microti* (ATCC #: 30221); *Entamoeba* spp., such as *Entamoeba histolytica* (ATCC #: 30015); *Eimeria* spp., such as *Eimeria maxima* (ATCC #40357); *Leishmania* spp., (Taxonomy ID: 38568); *Schistosome* spp., such as *Schistosoma mansoni* (GenBank accession # AZ301495); *Brugia* spp., such as *Brugia malayi* (GenBank accession # BE352806); *Fascida* spp., such as *Fasciola hepatica* (GenBank accession # AF286903); *Dirofilaria* spp., such as *Dirofilaria immitis* (GenBank accession # AF008300); *Wuchereria* spp., such as *Wuchereria bancrofti* (GenBank accession # AF250996); and *Onchocerea* spp; such as *Onchocerca volvulus* (GenBank accession # BE588251).

Examples of parasite antigens include, but are not limited to, the pre-erythrocytic stage antigens of *Plasmodium* spp. such as the circumsporozoite antigen of *P. falciparum* (GenBank accession # M22982) *P vivax* (GenBank accession # M20670); the liver stage antigens of *Plasmodium* spp, such as the liver stage antigen 1 (as referred to as LSA-1; GenBank accession # AF086802); the merozoite stage antigens of *Plasmodium* spp; such as the merozoite surface antigen-1 (also referred to as MSA-1 or MSP-1; GenBank accession # AF199410); the surface antigens of *Entamoeba histolytica*, such as the galactose specific lectin (GenBank accession # M59850) or the serine rich *Entamoeba histolytica* protein; the surface proteins of *Leishmania* spp, such as 63 kDa glycoprotein (gp63) of *Leishmania major* (GenBank accession # Y00647 or the 46 kDa glycoprotein (gp46) of *Leishmania major*; paramyosin of *Brugia malayi* (GenBank accession # U77590; the triose-phosphate isomerase of *Schistosoma mansoni* (GenBank accession # W06781; the secreted globin-like protein of *Trichostrongylus colubriformis* (GenBank accession # M63263; the glutathione-S-transferases of *Fasciola hepatica* (GenBank accession # M77682; *Schistosoma bovis* (GenBank accession # M77682); *S. japonicum* (GenBank accession # U58012; and KLH of *Schistosoma bovis* and *S. japonicum* (Bashir, et al., supra).

Examples of tumor specific antigens include prostate specific antigen (PSA), TAG-72 and CEA; human tyrosinase (GenBank accession # M27160); tyrosinase-related protein (also referred to as TRP; GenBank accession # AJ132933); and tumor-specific peptide antigens.

Examples of transplant antigens include the CD3 molecule on T cells and histocompatibility antigens such as HLA A, HLA B, HLA C, HLA DR and HLA.

Examples of autoimmune antigens include IAS β chain, which is useful in therapeutic vaccines against autoimmune encephalomyelitis (GenBank accession # D88762); glatamic acid decarboxylase, which is useful in therapeutic vaccines against insulin-dependent type 1 diabetes (GenBank accession # NM013445); thyrotropin receptor (TSHr), which is useful in therapeutic vaccines against Grave's disease (GenBank accession # NM000369) and tyrosinase-related protein 1, which is useful in therapeutic vaccines against vitiligo (GenBank accession # NM000550).

HIV drugs that may be used in the construction of the tagged antibodies or fragments thereof include, but are not limited to antiviral agents such as nucleoside RT inhibitors, CCR5 inhibitors/antagonists, viral entry inhibitors and their functional analogs. Specifically, an antiviral agent may nucleoside RT inhibitors, such as Zidovudine (ZDV, AZT), Lamivudine (3TC), Stavudine (d4T), Didanosine (ddl), Zalcitabine (ddC), Abacavir (ABC), Emirivine (FTC), Tenofovir (TDF), Delaviradine (DLV), Efavirenz (EFV), Nevirapine (NVP), Saquinavir (SQV), Ritonavir (RTV), Indinavir (IDV), Nelfinavir (NFV), Amprenavir (APV), Lopinavir (LPV), Atazanavir, Combivir (ZDV/3TC), Kaletra (RTV/LPV), Trizivir (ZDV/3TC/ABC);

CCR5 inhibitors/antagonists, such as SCH-C, SCH-D, PRO 140, TAK 779, TAK-220, RANTES analogs, AK602, UK-427, 857, monoclonal antibodies; and viral entry inhibitors, such as Fuzeon (T-20) (enfuvirtide), NB-2, NB-64, T-649, T-1249, SCH-C, SCH-D, PRO 140, TAK 779, TAK-220, RANTES analogs, AK602, UK-427, 857; and functional analogs or equivalents thereof.

It is envisioned that many different core fucosylated glycoproteins and nonfucosylated glycoproteins can be modified according to the methods of the present invention or used as a therapeutic agent for conjugation to a terminal sugar including but not limited to, adrenocorticotropic hormone (ACTH); adrenocorticotropic hormone derivatives (e.g., ebiratide); angiotensin; angiotensin II; asparaginase; atrial natriuretic peptides; atrial sodium diuretic peptides; bacitracin; beta-endorphins; blood coagulation factors VII, VIII and IX; blood thymic factor (FTS); blood thymic factor derivatives; bombesin; bone morphogenic factor (BMP); bone morphogenic protein; bradykinin; caerulein; calcitonin gene related polypeptide (CGRP); calcitonins; CCK-8; cell growth factors (e.g., EGF; TGF-alpha; TGF-beta; PDGF; acidic FGF; basic FGF); cerulein; chemokines; cholecystokinin; cholecystokinin-8; cholecystokinin-pancreozymin (CCK-PZ); colistin; colony-stimulating factors (e.g. CSF; GCSF; GMCSF; MCSF); corticotropin-releasing factor (CRF); cytokines; desmopressin; dinorphin; dipeptide; dismutase; dynorphin; eledoisin; endorphins; endothelin; endothelin-antagonistic peptides; endotherins; enkephalins; enkephalin derivatives; epidermal growth factor (EGF); erythropoietin (EPO); follicle-stimulating hormone (FSH); gallanin; gastric inhibitory polypeptide; gastrin-releasing polypeptide (GRP); gastrins; G-CSF; glucagon; glutathione peroxidase; glutathio-peroxidase; gonadotropins (e.g., human chorionic gonadotrophin and .alpha. and .beta. subunits thereof); gramicidin; gramicidines; growth factor (EGF); growth hormone-releasing factor (GRF); growth hormones; hormone releasing hormone (LHRH); human artrial natriuretic polypeptide (h-ANP); human placental lactogen; insulin; insulin-like growth factors (IGF-I; IGF-II); interferon; interferons (e.g., alpha- beta- and gamma-interferons); interleukins (e.g. 1; 2; 3; 4; 5; 6; 7; 8; 9; 10; 11 and 12); intestinal polypeptide (VIP); kallikrein; kyotorphin; luliberin; luteinizing hormone (LH); luteinizing hormone-releasing hormone (LH-RH); lysozyme chloride; melanocyte-stimulating hormone (MSH); melanophore stimulating hormone; mellitin; motilin; muramyl; muramyldipeptide; nerve growth factor (NGF); nerve nutrition factors (e.g. NT-3; NT-4; CNTF; GDNF; BDNF); neuropeptide Y; neurotensin; oxytocin; pancreastatin; pancreatic polypeptide; pancreozymin; parathyroid hormone (PTH); pentagastrin; polypeptide YY; pituitary adenyl cyclase-activating polypeptides (PACAPs); platelet-derived growth factor; polymixin B; prolactin; protein synthesis stimulating polypeptide; PTH-related protein; relaxin; renin; secretin; serum thymic factor; somatomedins; somatostatins derivatives; superoxide dismutase; taftsin; tetragastrin; thrombopoietin (TPO); thymic humoral factor (THF); thymopoietin; thymosin; thymostimulin; thyroid hormone releasing hormone; thyroid-stimulating hormone (TSH); thyrotropin releasing hormone TRH); trypsin; tuftsin; tumor growth factor (TGF-alpha); tumor necrosis factor (TNF); tyrocidin; urogastrone; urokinase; vasoactive intestinal polypeptide; and vasopressin.

Core fucosylated and nonfucosylated glycoproteins are important classes of biomolecules that play crucial roles in many biological events such as cell adhesion, tumor metastasis, pathogen infection, and immune response. As indicated previously herein, a major problem in structural and functional studies of fucosylated or nonfucosylated glycoproteins is their structural microheterogeneity. Natural and recombinant fucosylated or nonfucosylated glycoproteins are typically produced as a mixture of glycoforms that differ only in the structure of the pendent oligosaccharides.

The remodeled glycoproteins, such as antibodies can be subjected to any further structural modifications that are necessary or desired, including, without limitation, glycosyl transfer, and selective ligation (e.g., click chemistry, Staudinger reaction, etc.) to introduce the additional functional groups or tags. The functional groups can be of any suitable type, including, without limitation, toxins, special antigens (such as alpha-Gal), radioactive species, photoactive species, PEGs, etc. The glycoprotein can be catalytically reacted in a "click chemistry" cycloaddition reaction of the azide functionality of the glycoprotein with an alkyne bearing the functional moiety of interest. The azido and alkyne functional groups can be switched in the respective ligation components, and the glycoprotein can be functionalized with an alkynyl functionality and reacted with an azide-functionalized compound including the moiety of interest. It will also be appreciated that other ligation pairs can be devised for the click chemistry reaction.

The core fucosylated and nonfucosylated antibodies or fragments thereof, produced according to the methods described herein, can be used for diagnosis and therapeutics. Approximately two-thirds of therapeutic proteins, such as monoclonal antibodies used on the market and/or currently in clinical trials are glycoproteins. However, the structural heterogeneity in different glycoforms of natural and recombinant glycoproteins presents a major barrier in developing glycoprotein-based drugs, as different glycoforms may have different biological activities and controlling glycosylation to a homogeneous glycoform is extremely difficult during expression. The previous discovery of the transglycosylation activity of a class of endoglycosidases represents a major advance in the field for glycosylation engineering to enhance glycoproteins' therapeutic and diagnostic potentials and the Endo-S mutants of the present invention are able to transglycosylate core fucosylated and nonfucosylated natural and recombinant glycoproteins without the negative aspects of hydrolysis.

The features and advantages of the present invention are more fully shown by the following non-limiting examples.

EXAMPLES

Saturation site-directed mutagenesis of Endo-S at the Asp-233 site

Previous mutational and structural studies have shown that the Asp-233 is a critical residue that promotes the formation of the sugar oxazolinium ion intermediate during enzymatic catalysis[20, 27]. In particular, two mutants have been identified, D233A and D233Q, that are glycosynthases capable of using glycan oxazoline as an activated glycosyl donor substrate for the glycosylation reaction with diminished hydrolysis activity on the product[20]. In order to systematically screen for more efficient glycosynthase mutants of Endo-S, a library was constructed of Endo-S mutants by replacing the Asp-233 with the other 19 natural amino acids through saturation mutagenesis. The mutants were expressed and purified under the same conditions as for the wild-type Endo-S, and the yield of mutants (15-30 mg/L) were found to be comparable to that of the wild type Endo-S.

Comparison of Transglycosylation and Hydrolysis Activity of the Endo-S Mutants

The hydrolytic activity of the mutants generated was evaluated using rituximab as the substrate, and the transglycosylation activity was evaluated using the sugar oxazoline and the deglycosylated rituximab as the donor and acceptor substrates, respectively (Scheme 1). The results are summarized in Table 1. Comparison of the hydrolytic activity demonstrated that all 19 mutants, except for D233C, showed significantly diminished hydrolysis activity on the whole antibody in comparison with wild type Endo-S. Interestingly, the D233C (SEQ ID NO: 5) showed a similar hydrolysis activity as the wild-type Endo-S.

Among the mutants D233H, D233K, D233R, D233P, D233W and D233Y of SEQ ID NO: 1 showed less than 0.5% of the intrinsic hydrolytic activity of the wild-type Endo-S, whereas D233C still retained a significant capacity to hydrolyze the antibody Fc N-glycans at Asn-297. On the other hand, the transglycosylation assay revealed that most Endo-S mutants were able to transfer a biantennary complex-type glycan oxazoline to a deglycosylated rituximab antibody with varied efficiencies. In particular, D233C (SEQ ID NO: 5), D233E (SEQ ID NO: 6), D233G (SEQ ID NO: 7), D233M (SEQ ID NO: 2) and D233N (SEQ ID NO: 8) demonstrated the most significant transglycosylation activities, while the mutants D233F, D233I, and D233L of SEQ ID NO: 1 had only marginal transglycosylation activity. However, by comparing the overall transglycosylation efficiencies, most mutants with potent transglycosylation activities also possessed residual hydrolysis activity, a property less ideal for antibody glycosylation remodeling. For instance, D233C (SEQ ID NO: 5) showed the highest activity for both hydrolysis and transglycosylation among all the mutants, but its overall efficiency for glycoform synthesis (defined by the ratio of transglycosylation/hydrolysis, T/H) was only moderate. Interestingly, D233M (SEQ ID NO: 2) mutant demonstrated a relatively high transglycosylation activity among the mutants with a remarkably low residual hydrolysis activity. Thus, the highest overall synthetic efficiency makes D233M the most efficient glycosynthase mutant of Endo-S for antibody glycoengineering among the mutants. Based on the results of transglycosylation and residual hydrolysis activities of the mutants (Table 1), D233M showed an approximately 3- and 8-fold enhanced synthetic efficiency (T/H) over the previously reported Endo-S mutants, D233Q (SEQ ID NO: 3) and D233A (SEQ ID NO: 4), respectively[20]. To demonstrate the improved catalytic efficiency of the Endo-S D233M mutant for the antibody Fc glycan remodeling, the transglycosylation reaction of the three selected mutants, D233M, D233Q and D233A was compared with the glycan oxazoline under the same glycosylation conditions. The parallel reactions were monitored by LC-ESI-MS (FIG. 1). The time-course of the glycosylation indicated that mutant D233M was more efficient than the previously identified mutants, D233A and D233Q[20].

Kinetic analysis of Endo-S D233M and Endo-S D233A

Figure 2:
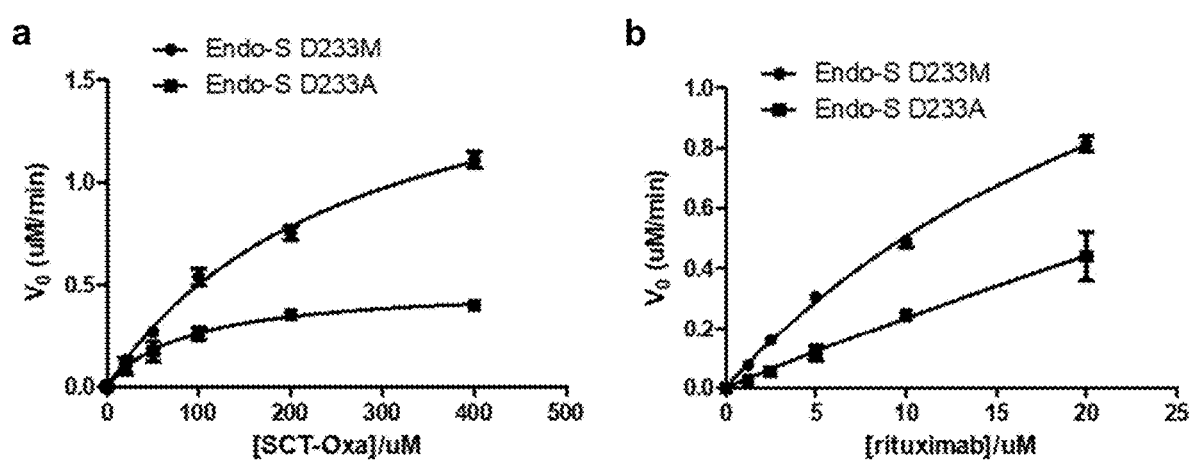
FIG. 2 shows Michaelis-Menten plots of Endo-S mutants (D233M and D233A) for the substrates. a) for the donor substrate (glycan oxazoline SCT-Oxa); b) for the acceptor substrate (the deglycosylated rituximab). The data sets presented here are representative of three independent experiments.

The observed difference in the catalytic activity of D233M and D233A mutants was the impetus to perform a kinetic analysis of the two mutants. Using a sialylated glycan oxazoline (SCT-Oxa) as the donor and the deglycosylated rituximab as the acceptor substrate, we measured the kinetic parameters of the enzyme catalyzed glycosylation were measured. A mass spectrometry-based approach with an internal standard was used to estimate the product formation.[31-33] The results are summarized in Tables 2 and 3. For the biantennary complex-type glycan oxazoline (SCT-Oxa), the catalytic efficiency of Endo-S D233M ($k_{cat}/K_M$=0.03 min$^{-1}$ μM$^{-1}$) showed a 3-fold increase in comparison with that of Endo-S D233A ($k_{cat}/K_M$=0.01 min$^{-1}$ μM$^{-1}$) (Table 2 and FIG. 2a). The apparent increase in $k_{cat}/K_M$ of Endo-S D233M over D233A was a result of approximately 4-fold increase in turnover (as measured by $k_{cat}$) and a less than 2-fold reduced affinity as estimated by the $K_M$ value, as a higher $K_M$ value is indicative of a lower substrate affinity. These results suggested that substitution with a methionine instead of an alanine at Asp-233 enhanced the enzymatic turnover number with a moderate decrease on the substrate affinity for the glycan oxazoline substrate.

TABLE 2

Kinetic parameters of Endo-S mutants
Endo-S D233M and D233A for SCT-Oxa

| Enzyme | $k_{cat}$ (min$^{-1}$) | $K_M$ (μM) | $k_{cat}/K_M$ (min$^{-1}$ μM$^{-1}$) |
|---|---|---|---|
| Endo-S D233M | 4.99 ± 0.91 | 195.40 ± 7.21 | 0.03 |
| Endo-S D233A | 1.34 ± 0.19 | 87.91 ± 10.13 | 0.01 |

For the glycosyl acceptor substrate, the deglycosylated antibody, the Endo-S D233M mutant showed a much higher substrate affinity than the D233A mutant. This was clearly supported by the Michaelis-Menten curves of the two mutants (FIG. 2b), which demonstrated that Endo-S D233M was much easier to saturate than the D233A mutant by the antibody substrate. The $K_M$ of D233M for the deglycosylated antibody was 30 μM, while the $K_M$ of D233A for the deglycosylated antibody was >200 μM (Table 3) On the other hand, the catalytic turnover number of Endo-S D233A ($k_{cat}$) for the antibody substrate could not be accurately measured because the concentration of the deglycosylated antibody required to saturate the enzyme was difficult to achieve.

TABLE 3

Kinetic parameters of Endo-S mutants
Endo-S D233M and D233A for rituximab

| Enzyme | $k_{cat}$ (min$^{-1}$) | $K_M$ (μM) | $k_{cat}/K_M$ (min$^{-1}$ μM$^{-1}$) |
|---|---|---|---|
| Endo-S D233M | 5.53 ± 1.91 | 30.22 ± 7.21 | 0.18 |
| Endo-S D233A | —* | >200 | —* |

*The catalytic turnover number of Endo-S D233A could not be accurately determined by the software due to the fact that the concentration required for enzyme saturation exceeded the limits of the solubility of the deglycosylated antibody in solution.

Kinetic analysis of Endo-S2 D184M and Endo-S2 D184A

Figure 3:
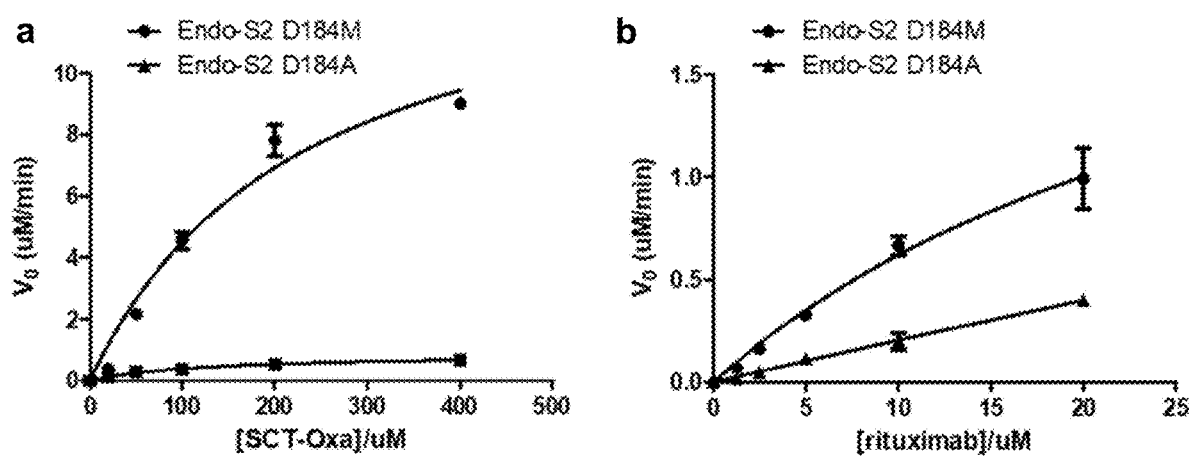
FIG. 3 shows Michaelis-Menten plots of Endo-S2 mutants (D184M and D184A) for the substrates. a) for the donor substrate (sugar oxazoline SCT-Oxa); b) for the acceptor substrate (the deglycosylated rituximab). The data sets presented here are representative of three independent experiments.
Figure 4:
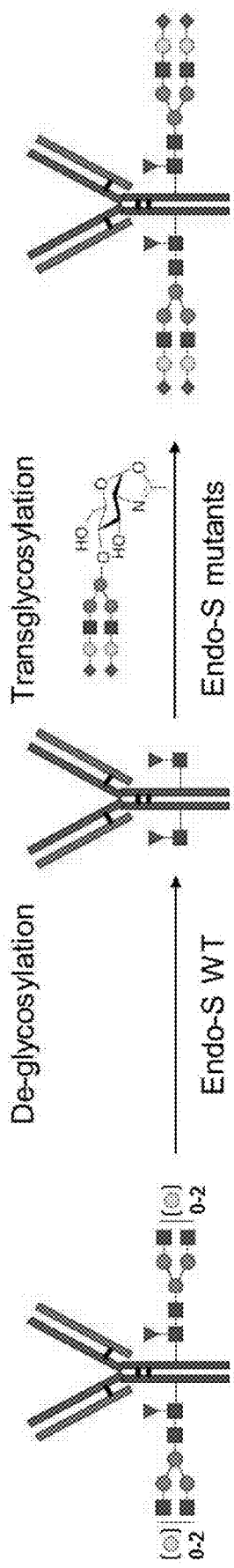
FIG. 4 shows a schematic presentation of the hydrolysis and transglycosylation by Endo-S and its mutants using commercial antibody rituximab as the substrate

Endo-S2 is another endoglycosidase from *Streptococcus pyogenes* serotype M49 that shows much broader substrate specificity than Endo-S for antibody degycosylation[30]. A recent study on the mutations at the critical Asp-184 residue has identified the D184M mutant as the most efficient glycosynthase mutant within the systematic library of Endo-S2 variants generated through saturation mutagenesis[29]. To evaluate the nature of the enhanced catalytic efficiency, the kinetic parameters of D184M and D184A mutants of wild type Endo-S2 (SEQ ID NO: 11) were also measured. The results revealed a similar pattern between the Endo-S and Endo-S2 mutants. For the sugar oxazoline substrate, the Endo-S2 methionine mutation significantly enhanced the catalytic efficiency ($k_{cat}/K_M$) in comparison with the alanine mutation, and a more than 10-fold increase in $k_{cat}/K_M$ value was observed for the D184M mutant over the D184A mutant (Table 4 and FIG. 3a). In analogy to Endo-S, the increased $k_{cat}/K_M$ value for D184M mutant was caused by a more than 15-fold increase in catalytic turnover numbers ($k_{cat}$) and a less than 2-fold decrease in substrate affinity ($K_M$) for the glycan oxazoline substrate.

For the deglycosylated rituximab, like the Endo-S D233M mutant, the Endo-S2 D184M mutant also showed a significantly higher substrate affinity for the antibody than the Endo-S2 D184A mutant. The $K_M$ value of Endo-S2 D184A was estimated to be more than 20 times higher than that of the Endo-S2 D184M. Similar to the case of Endo-S, Michaelis-Menten curves also indicated that the Endo-S2 D184A mutant showed no sign of saturation within the range of concentrations of antibody tested. Therefore, the catalytic turnover number of the Endo-S2 D184A also couldn't be accurately measured due to the difficulty to reach a saturated concentration of the substrate (Table 5 and FIG. 3b).

Interestingly, for both the sugar oxazoline and the antibody substrates, Endo-S2 D184M demonstrated a significantly higher catalytic turnover number than Endo-S D233M, whereas the substrate affinity for both substrates proved to be comparable between the two mutants. Therefore, the overall catalytic efficiency ($k_{cat}/K_M$) of Endo-S2 D184M was found to be higher than that of Endo-S D233M.

TABLE 4

Kinetic parameters of Endo-S2 mutants
D184M and D184A for SCT-Oxa

| Enzyme | $k_{cat}$ (min$^{-1}$) | $K_M$ (μM) | $k_{cat}/K_M$ (min$^{-1}$ μM$^{-1}$) |
|---|---|---|---|
| Endo-S2 D184M | 167.81 ± 20.50 | 229.10 ± 34.80 | 0.73 |
| Endo-S2 D184A | 10.20 ± 2.37 | 121.31 ± 17.14 | 0.08 |

TABLE 5

Kinetic parameters of Endo-S2 mutants
D184M and D184A for rituximab

| Enzyme | $k_{cat}$ (min$^{-1}$) | $K_M$ (μM) | $k_{cat}/K_M$ (min$^{-1}$ μM$^{-1}$) |
|---|---|---|---|
| Endo-S2 D184M | 29.84 ± 9.30 | 32.62 ± 6.71 | 0.91 |
| Endo-S2 D184A | —* | >680 | —* |

*The catalytic turnover number of Endo-S D233A could not be accurately determined by the software due to the fact that the concentration required for enzyme saturation exceeded the limits of the solubility of the deglycosylated antibody in solution.

DISCUSSION

Two glycosynthase mutants, D233A and D233Q of Endo-S have been previously identified, which could transfer glycan oxazoline to Fc-deglycosylated antibody to form homogeneous antibody glycoforms[20]. More recently, new glycosynthase mutants from Endo-S2 have been identified by mutation at the critical Asp-184 residue, which show broader substrate specificity and distinct efficiency for antibody Fc glycan remodeling[29]. However, a systematic mutagenesis on prototype enzyme Endo-S at the critical Asp-233 site had not been studied and the mechanism behind the observed difference in catalysis by different mutants remained to be characterized. In the present work, a systematic mutagenesis of Endo-S was performed by generating all the 19 natural amino acid mutants at the Asp-233 residue of Endo-S and examined their residual hydrolysis activity and transglycosylation activity. The present invention identified several novel glycosynthase mutants of Endo-S such as the D233M mutant that demonstrated enhanced transglycosylation activity with diminished hydrolysis of product. The kinetic analysis revealed that the enhanced catalytic efficiency of the Endo-S2 D184M mutant over the D184A mutant contributed mainly by two factors: the increased turnover for the glycan oxazoline donor substrate and the enhanced affinity for the antibody substrate. This is also true for the observed enhanced catalytic efficacy of the Endo-S D233M mutant over the Endo-S D233A mutant. It is still not clear how the methionine mutation leads to the increased turnover of the glycan oxazoline substrate and the enhanced affinity for the antibody substrate. The crystal structure of Endo-S enzyme and more recently the crystal structure of the Endo-S2 in complex with a complex type N-glycan were solved[27, 28]. But, unfortunately, the structure of the Endo-S2 or Endo-S complexed with an antibody Fc domain remains to be solved, which may provide an answer to the role of the methionine mutation at the critical D184 (for Endo-S2) or D233 (for Endo-S) residue in improving the glycosynthase activity.

CONCLUSION

It was found herein that in addition to the previously identified D233A and D233Q mutants of Endo-S, most of the Asp-233 mutants discovered here were also glycosynthases that demonstrated glycosylation activity using glycan oxazoline as the donor substrate with diminished hydrolysis activity. The glycosynthase activity of the resultant mutants varied significantly depending on the nature of the amino acid substituents. Among them, the D233M mutant was identified as the most efficient glycosynthase variant with the highest transglycosylation/hydrolysis ratio. Kinetic studies on the D233M and D233A mutants of Endo-S indicated that the enhanced catalytic efficacy of the Asp-to-Met mutant was mainly due to increased turnover (kcat) for the glycan oxazoline substrate and the significantly enhanced affinity (as judged by the reduced $K_M$ value) for the antibody acceptor, respectively.

Methods and Material

Monoclonal antibody, rituximab, was purchased from Genentech Inc., (South San Francisco, Calif.). Sialoglycan complex-type oxazolines were chemically synthesized according to the previously published procedure[34]. The wild-type Endo-S/S2 and mutants were expressed and purified according to protocols from our previous studies[20].

Site-directed mutagenesis, expression and purification of recombinant Endo-S and mutants The pGEX plasmid vector encoding the wild-type Endo-S was a gift from Dr. M. Collin (Lund University, Sweden). The Endo-S mutants were generated using the Q5 Site-Directed Mutagenesis Kit (NEB) by the manufacturer's instructions. For systematic mutagenesis at Asp-233, two degenerate primers were used: 5' CGTAAATTCGTGCT-CAATNNNAATATCTAG TCCATCGACACCACGATCA-GTT-3' (forward) (SEQ ID NO: 9) and 5'-AACT-GATCGTGGTGTCGATGGACTAGATATTNNNATTGAG CACGAATTTACG-3' (SEQ ID NO: 10) (Reverse). Mutations were verified by DNA sequencing. The plasmid DNA encoding the wild type and mutant Endo-S genes was transformed in E. coli BL21 (DE3) cells for overexpression.

For simultaneous purification of all 20 Endo-S enzymes, the transformed cells were grown in 20 mL 2YT media with 100 μg/mL Carbenicillin added. Cells were incubated at 37° C. and induced with 0.5 mM isopropyl β-D-1-thiogalactopyranoside (IPTG) when they reached an OD600 of 0.8-1.0. The induced cells were incubated at 20° C. overnight and harvested by centrifugation. The cell lysates were collected after treating with bacterial cell lysis buffer (Gold Biotechnology, Inc.) following manufacturer's instructions. The GST-tagged proteins were purified using the GST Spin Column Kit (Thermo). The purified proteins were diluted into PBS at pH 7.4 after buffer exchange using Amicon ultra filtration units (10 kDa, Millipore). The purity of EndoS proteins was over 90% on SDS-PAGE and the final concentration was recorded on a NanoDrop 2000c at absorbance 280 nm. The expression and purification of Endo-S2 mutants were performed following our recent publication[20]. Both enzymes and their mutants showed similar expression yield and purity (>90%).

Synthesis of the Fucα1,6GlcNAc-Rituximab Through the Wild-Type Endo-S Deglycosylation In order to generate deglycosylated rituximab for transglycosylation assays, commercial antibody was treated with the wild-type Endo-S at a substrate-to-enzyme ratio of 1000:1 (w/w) for 30 min at 37° C. to release the heterogeneous N-glycoforms. Complete hydrolysis of glycans was confirmed by LC-MS analysis. The product GlcNAc-rituximab was subsequently purified through protein-A affinity chromatography. The deconvoluted mass (m/z) of purified antibody corresponds well to the calculated mass of Fucα1,6 GlcNAc-rituximab.

Liquid Chromatography Mass Spectrometry (LC-ESI-MS) Analysis of IgG Antibody

The LC-MS characterization of different antibody glycoforms was conducted on an Exactive Plus Orbitrap instrument (Thermo Scientific). The intact antibody sample was analyzed with a Waters XBridge™ BEH300 C4 column (3.5 μm, 2.1×50 mm). The program includes a 9 min linear gradient of 5-90% MeCN containing 0.1% formic acid at a flow rate of 0.4 mL/min. The original mass data were processed through deconvolution and integration through MagTran Software (Amgen).

Quantification Using an Internal Standard and Single-Point Normalization Factor

Peptide-N-Glycosidase F (PNGase F) treated rituximab was used as the internal standard due to its similarities to the deglycosylated and transferred product in terms of their molecular structures and ionization efficiencies. After PNGase F treatment, a mutation will be introduced into the amino acid sequence of rituximab so the product antibody will not interfere with the reaction via re-glycosylation[35]. A standard product S2G2F-rituximab was synthesized following the previously reported procedure[29]. ESI-MS spectra indicated that the starting material had been completely converted to the transglycosylation product. Serial dilutions containing a gradient of S2G2F-rituximab (0, 0.25, 0.5, 0.75, 1.0, 1.25 and 1.5 μM) were mixed with a stock solution containing 0.67 μM internal standard. These mixed sample solutions were quantified by selected ion monitoring (SIM) to calculate the single-point normalization factor[31]. The factor could then be used to calculate the relative amount of the final product N-glycoform for each reaction in the following experiments.

Transglycosylation and Hydrolysis Activity Assays

The hydrolytic activity of each Endo-S mutants and the wild-type (0.01 mg/mL) was assayed in PBS (pH 7.4, 10 μl) at 30° C. with synthetic biantennary sialo-complex-type rituximab (1.0 mg/mL, 6.9 μM) as the starting material. Each reaction was terminated at 5 min and an aliquot was taken from the reaction mixture and dissolved in 0.1% formic acid. The relative quantity of the hydrolysis product was calculated through deconvolution and integration of the selected MS peaks. The experimental details of product quantification using LC-MS are illustrated below. The transglycosylation activity of Endo-S was measured in a similar fashion: deglycosylated Rituximab (10.0 mg/mL, 69 μM) was incubated with SCT-Oxa (1.38 mM, 20 eq) under catalysis of Endo-S enzymes (0.01 mg/mL) under the same condition as hydrolysis. The transglycosylation product SCT-Rituximab was analyzed as mentioned above. Both functional assays were repeated twice for each mutant and the wild-type, and the average activity was recorded Kinetic Measurements for the Endo-S and Endo-S2 Mutants Measurements of $K_M$ and Vmax for SCT-oxa. Serial dilutions with a total volume of 10 μL were prepared with a gradient of SCT-oxa concentrations and a constant deglycosylated antibody concentration mixed in PBS, pH 7.4. Each reaction was initiated by adding 1μμL, of Endo-S/S2 mutants with a concentration of 0.1 mg/Ml and the reaction was conducted at 30° C. The concentrations of SCT-oxa were within a range from 6.25 μM to 400 μM. For each reaction, three aliquots were taken at t=1, 2 and 3 min and immediately quenched in 100 μL 0.1% formic acid. The quenched reaction samples were then characterized by ESI-MS, and the concentration of product in each mixture was calculated using the normalization factor, as shown above. A linear progression curve was confirmed for each reaction by sampling at multiple early time points and plotting them in the same graph, which emphasized that the $V_0$ measured indeed represents the initial rate of each reaction. The $K_M$ and Vmax were measured by fitting the initial velocity against the SCT-oxa concentration using the GraphPad Prism7 program. The experiments were conducts in triplicate to determine the error in these measurements. A control reaction without the enzyme was set up for each reaction to confirm that non-enzymatic transfer of SCT-Oxa to the antibody did not happen and the results obtained here indeed represent the specific activity of each mutant.

Measurements of $K_M$ and Vmax for the Deglycosylated Rituximab.

The $K_M$ and Vmax values of both Endo-S and Endo-S2 mutants for the deglycosylated antibody substrate were measured in a similar fashion as to those for SCT-Oxa. In the serial reactions, the concentrations of antibody range from 0.313 μM to 20 μM, whereas the SCT-Oxa concentration was fixed at 400 μM. A similar control reaction was also performed for each concentration to monitor the non-enzymatic side reactions.

TABLE 1

Comparison of the specific transglycosylation efficiencies of the Endo-S D233 mutants measured by LC-ESI-MS using commercial rituximab as the substrate. The experiments were conducted in duplicate.

| Endo-S Mutants | Specific Hydrolysis Activity 100*(μmol/min/mg) | Transglycosylation Activity 100*(μmol/min/mg) | Transglycosylation/ Hydrolysis Ratio T/H |
|---|---|---|---|
| WT | 2.77 | 25.89 | 9.35 |
| D233A | 0.06 | 1.06 | 17.67 |
| D233C | 0.92 | 21.29 | 23.14 |
| D233E | 0.36 | 9.45 | 26.25 |
| D233F | 0.02 | 0.16 | 8.00 |
| D233G | 0.25 | 3.13 | 12.52 |
| D233H | 0.01 | 0.00 | 0.00 |
| D233K | 0.01 | 0.00 | 0.00 |
| D233R | 0.01 | 0.00 | 0.00 |
| D233I | 0.04 | 0.14 | 3.50 |
| D233L | 0.02 | 0.14 | 7.00 |
| D233M | 0.02 | 2.71 | 135.50 |
| D233N | 0.43 | 2.96 | 6.88 |
| D233P | 0.02 | 0.00 | 0.00 |
| D233Q | 0.05 | 0.98 | 19.60 |
| D233S | 0.36 | 3.65 | 10.14 |
| D233T | 0.21 | 1.79 | 8.52 |
| D233V | 0.21 | 0.25 | 1.19 |
| D233W | 0.01 | 0.00 | 0.00 |
| D233Y | 0.01 | 0.26 | 26.00 |

The references cited herein are incorporated by reference herein for all purposes.

[1] Elvin, J. G., Couston, R. G., and van der Walle, C. F. (2013) Therapeutic antibodies: market considerations, disease targets and bioprocessing, Int J Pharm 440, 83-98.

[2] Bhati, M., and Bandyopadhyay, S. (2016) Efficacy and safety of an anti-CD20 monoclonal antibody (Reditux) for the treatment of patients with moderate to severe rheumatoid arthritis following the failure of conventional synthetic disease-modifying anti-rheumatic drugs, Clin Rheumatol 35, 1931-1935.

[3] Cao, K., Pan, Y., Yu, L., Shu, X., Yang, J., Sun, L., Sun, L., Yang, Z., and Ran, Y. (2017) Monoclonal antibodies targeting non-small cell lung cancer stem-like cells by multipotent cancer stem cell monoclonal antibody library, Int J Oncol 50, 587-596.

[4] Arnold, J. N., Wormald, M. R., Sim, R. B., Rudd, P. M., and Dwek, R. A. (2007) The Impact of Glycosylation on the Biological Function and Structure of Human Immunoglobulins, Annu. Rev. Immunol. 25, 21-50.

[5] Li, W., Yu, R., Ma, B., Yang, Y., Jiao, X., Liu, Y., Cao, H., Dong, W., Liu, L., Ma, K., et al. (2015) Core fucosylation of IgG B cell receptor is required for antigen recognition and antibody production, J Immunol 194, 2596-2606.

[6] Peipp, M., Lammerts van Bueren, J. J., Schneider-Merck, T., Bleeker, W. W., Dechant, M., Beyer, T., Repp, R., van Berkel, P. H., Vink, T., van de Winkel, J. G., et al. (2008) Antibody fucosylation differentially impacts cytotoxicity mediated by NK and PMN effector cells, Blood 112, 2390-2399.

[7] Scallon, B., McCarthy, S., Radewonuk, J., Cai, A., Naso, M., Raju, T. S., and Capocasale, R. (2007) Quantitative in vivo comparisons of the Fc gamma receptor-dependent agonist activities of different fucosylation variants of an immunoglobulin G antibody, Int Immunopharmacol 7, 761-772.

[8] Campbell, I. K., Miescher, S., Branch, D. R., Mott, P. J., Lazarus, A. H., Han, D., Maraskovsky, E., Zuercher, A. W., Neschadim, A., Leontyev, D., et al. (2014) Therapeutic effect of IVIG on inflammatory arthritis in mice is dependent on the Fc portion and independent of sialylation or basophils, *J Immunol* 192, 5031-5038.

[9] Schwab, I., and Nimmerjahn, F. (2014) Role of sialylation in the anti-inflammatory activity of intravenous immunoglobulin-F(ab')(2) versus Fc sialylation, *Clin. Exp. Immunol.* 178 *Suppl* 1, 97-99.

[10] Washburn, N., Schwab, I., Ortiz, D., Bhatnagar, N., Lansing, J. C., Medeiros, A., Tyler, S., Mekala, D., Cochran, E., Sarvaiya, H., et al. (2015) Controlled tetra-Fc sialylation of IVIg results in a drug candidate with consistent enhanced anti-inflammatory activity, *Proc. Natl. Acad. Sci. USA* 112, E1297-1306.

[11] Damen, C. W., Chen, W., Chakraborty, A. B., van Oosterhout, M., Mazzeo, J. R., Gebler, J. C., Schellens, J. H., Rosing, H., and Beijnen, J. H. (2009) Electrospray ionization quadrupole ion-mobility time-of-flight mass spectrometry as a tool to distinguish the lot-to-lot heterogeneity in N-glycosylation profile of the therapeutic monoclonal antibody trastuzumab, *J Am Soc Mass Spectrom* 20, 2021-2033.

[12] Olivova, P., Chen, W., Chakraborty, A. B., and Gebler, J. C. (2008) Determination of N-glycosylation sites and site heterogeneity in a monoclonal antibody by electrospray quadrupole ion-mobility time-of-flight mass spectrometry, *Rapid Commun Mass Spectrom* 22, 29-40.

[13] Niwa, R., Shoji-Hosaka, E., Sakurada, M., Shinkawa, T., Uchida, K., Nakamura, K., Matsushima, K., Ueda, R., Hanai, N., and Shitara, K. (2004) Defucosylated chimeric anti-CC chemokine receptor 4 IgG1 with enhanced antibody-dependent cellular cytotoxicity shows potent therapeutic activity to T-cell leukemia and lymphoma, *Cancer Res.* 64, 2127-2133.

[14] Illidge, T., Cheadle, E. J., Donaghy, C., and Honeychurch, J. (2014) Update on obinutuzumab in the treatment of B-cell malignancies, *Expert Opin Biol Ther* 14, 1507-1517.

[15] Yamane-Ohnuki, N., Kinoshita, S., Inoue-Urakubo, M., Kusunoki, M., Iida, S., Nakano, R., Wakitani, M., Niwa, R., Sakurada, M., Uchida, K., et al. (2004) Establishment of FUT8 knockout Chinese hamster ovary cells: an ideal host cell line for producing completely defucosylated antibodies with enhanced antibody-dependent cellular cytotoxicity, *Biotechnol. Bioeng.* 87, 614-622.

[16] Stanley, P., Sundaram, S., Tang, J., and Shi, S. (2005) Molecular analysis of three gain-of-function CHO mutants that add the bisecting GlcNAc to N-glycans, *Glycobiology* 15, 43-53.

[17] Cox, K. M., Sterling, J. D., Regan, J. T., Gasdaska, J. R., Frantz, K. K., Peele, C. G., Black, A., Passmore, D., Moldovan-Loomis, C., Srinivasan, M., et al. (2006) Glycan optimization of a human monoclonal antibody in the aquatic plant *Lemna minor*, *Nat. Biotechnol.* 24, 1591-1597.

[18] Wei, Y., Li, C., Huang, W., Li, B., Strome, S., and Wang, L. X. (2008) Glycoengineering of human IgG1-Fc through combined yeast expression and in vitro chemoenzymatic glycosylation, *Biochemistry* 47, 10294-10304.

[19] Zou, G., Ochiai, H., Huang, W., Yang, Q., Li, C., and Wang, L. X. (2011) Chemoenzymatic synthesis and Fcgamma receptor binding of homogeneous glycoforms of antibody Fc domain. Presence of a bisecting sugar moiety enhances the affinity of Fc to FcgammaIIIa receptor, *J Am. Chem. Soc.* 133, 18975-18991.

[20] Huang, W., Giddens, J., Fan, S. Q., Toonstra, C., and Wang, L. X. (2012) Chemoenzymatic glycoengineering of intact IgG antibodies for gain of functions, *J. Am. Chem. Soc.* 134, 12308-12318.

[21] Giddens, J. P., Lomino, J. V., Amin, M. N., and Wang, L. X. (2016) Endo-F3 Glycosynthase Mutants Enable Chemoenzymatic Synthesis of Core-fucosylated Triantennary Complex Type Glycopeptides and Glycoproteins, *J. Biol. Chem.* 291, 9356-9370.

[22] Liu, R., Giddens, J., McClung, C. M., Magnelli, P. E., Wang, L. X., and Guthrie, E. P. (2016) Evaluation of a glycoengineered monoclonal antibody via LC-MS analysis in combination with multiple enzymatic digestion, *MAbs* 8, 340-346.

[23] Parsons, T. B., Struwe, W. B., Gault, J., Yamamoto, K., Taylor, T. A., Raj, R., Wals, K., Mohammed, S., Robinson, C. V., Benesch, J. L., et al. (2016) Optimal Synthetic Glycosylation of a Therapeutic Antibody, *Angew. Chem. Int. Ed.* 55, 2361-2367.

[24] Lin, C. W., Tsai, M. H., Li, S. T., Tsai, T. I., Chu, K. C., Liu, Y. C., Lai, M. Y., Wu, C. Y., Tseng, Y. C., Shivatare, S. S., et al. (2015) A common glycan structure on immunoglobulin G for enhancement of effector functions, *Proc. Natl. Acad. Sci. USA* 112, 10611-10616.

[25] Kurogochi, M., Mori, M., Osumi, K., Tojino, M., Sugawara, S., Takashima, S., Hirose, Y., Tsukimura, W., Mizuno, M., Amano, J., et al. (2015) Glycoengineered Monoclonal Antibodies with Homogeneous Glycan (M3, G0, G2, and A2) Using a Chemoenzymatic Approach Have Different Affinities for FcgammaRIIIa and Variable Antibody-Dependent Cellular Cytotoxicity Activities, *PLoS One* 10, e0132848.

[26] Tong, X., Li, T., Orwenyo, J., Toonstra, C., and Wang, L. X. (2018) One-pot enzymatic glycan remodeling of a therapeutic monoclonal antibody by endoglycosidase S (Endo-S) from *Streptococcus pyogenes*, *Bioorg Med Chem* 26, 1347-1355.

[27] Trastoy, B., Lomino, J. V., Pierce, B. G., Carter, L. G., Gunther, S., Giddens, J. P., Snyder, G. A., Weiss, T. M., Weng, Z., Wang, L. X., et al. (2014) Crystal structure of *Streptococcus pyogenes* EndoS, an immunomodulatory endoglycosidase specific for human IgG antibodies, *Proc Natl Acad Sci USA* 111, 6714-6719.

[28] Trastoy, B., Klontz, E., Orwenyo, J., Marina, A., Wang, L. X., Sundberg, E. J., and Guerin, M. E. (2018) Structural basis for the recognition of complex-type N-glycans by Endoglycosidase S, *Nat Commun* 9, 1874.

[29] Li, T., Tong, X., Yang, Q., Giddens, J. P., and Wang, L. X. (2016) Glycosynthase Mutants of Endoglycosidase S2 Show Potent Transglycosylation Activity and Remarkably Relaxed Substrate Specificity for Antibody Glycosylation Remodeling, *J. Biol. Chem.* 291, 16508-16518.

[30] Sjogren, J., Cosgrave, E. F., Allhorn, M., Nordgren, M., Bjork, S., Olsson, F., Fredriksson, S., and Collin, M. (2015) EndoS and EndoS2 hydrolyze Fc-glycans on therapeutic antibodies with different glycoform selectivity and can be used for rapid quantification of high-mannose glycans, *Glycobiology* 25, 1053-1063.

[31] Pi, N., Armstrong, J. I., Bertozzi, C. R., and Leary, J. A. (2002) Kinetic analysis of NodST sulfotransferase using an electrospray ionization mass spectrometry assay, *Biochemistry* 41, 13283-13288.

[32] Ge, X., Sirich, T. L., Beyer, M. K., Desaire, H., and Leary, J. A. (2001) A strategy for the determination of enzyme kinetics using electrospray ionization with an ion trap mass spectrometer, *Anal Chem* 73, 5078-5082.

[33] Danan, L. M., Yu, Z., Hoffhines, A. J., Moore, K. L., and Leary, J. A. (2008) Mass spectrometric kinetic analysis of human tyrosylprotein sulfotransferase-1 and -2, *J Am Soc Mass Spectrom* 19, 1459-1466.

[34] Aikawa, J., Takeda, Y., Matsuo, I., and Ito, Y. (2014) Trimming of glucosylated N-glycans by human ER alpha1,2-mannosidase I, *J Biochem* 155, 375-384.

[35] Bodnar, J., Szekrenyes, A., Szigeti, M., Jarvas, G., Krenkova, J., Foret, F., and Guttman, A. (2016) Enzymatic removal of N-glycans by PNGase F coated magnetic microparticles, *Electrophoresis* 37, 1264-1269.

That which is claimed is:

1. A method of preparing a core fucosylated or nonfucosylated antibody or Fc fragment thereof having a predetermined oligosaccharide moiety, the method comprising:
providing an antibody or Fc fragment comprising a core fucosylated or nonfucosylated GlcNAc-acceptor; and enzymatically reacting the core fucosylated or nonfucosylated GlcNAc-acceptor with an activated oligosaccharide donor using a *Streptococcus pyogenes* Endoglycosidase-S Asp233 mutant having an amino acid sequence comprising SEQ ID NO: 2 (D233M), wherein the activated oligosaccharide donor carries an oligosaccharide moiety comprising a predetermined number and type of sugar residues, wherein via an enzymatic reaction, the activated oligosaccharide moiety is covalently linked to the core fucosylated or nonfucosylated GlcNAc-acceptor, thereby preparing the fucosylated or nonfucosylated antibody or Fc fragment having the predetermined oligosaccharide moiety.

2. The method of claim 1, wherein the activated oligosaccharide component is a synthetic oligosaccharide oxazoline or sialylated oxazoline.

3. The method of claim 1, wherein the synthetic oligosaccharide oxazoline is a di-, tri-, tetra-, penta-, hexyl-, hepta-, octyl-, nona-, deca- or undeca-saccharide oxazoline.

4. The method of claim 1, wherein the activated oligosaccharide component further comprises an additional biologically active agent or a tag.

5. The method of claim 4, wherein the additional biologically active agent or tag is a drug, toxin, fluorescent probe, biotin, a PEG, lipid, or polypeptide.

6. The method of claim 1, wherein the fucosylated GlcNAc-acceptor is an alpha-1-6-fucosyl-GlcNAc-protein.

7. The method of claim 1, wherein the core fucosylated or nonfucosylated antibody is a monoclonal antibody selected from the group consisting of 17b, 48d, A32, C11, 2G12, F240, IgG1b12, 19e, X5, TNX-355, cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, I-131 tositumomab, efalizumab, bevacizumab, panitumumab, pertuzumab, natalizumab, etanercept, IGN101, volociximab, Anti-CD80 mAb, Anti- CD23 mAb, CAT-3888, CDP-791, eraptuzumab, MDX-010, MDX-060, MDX-070, matuzumab, CP-675,206, CAL, SGN-30, zanolimumab, adecatumumab, oregovomab, nimotuzumab, ABT-874, denosumab, AM 108, AMG 714, fontolizumab, daclizumab, golimumab, CNTO 1275, ocrelizumab, HuMax-CD20, belimumab, epratuzumab, MLN1202, visilizumab, tocilizumab, ocrerlizumab, certolizumab pegol, eculizumab, pexelizumab, abciximab, ranibizimumab, mepolizumab and MYO-029.

8. The method of claim 1, wherein the antibody further comprises an additional moiety selected from a group consisting of a therapeutic agent for treating cancer, a therapeutic agent for HIV, a toxin, an antibody different from the modified antibody which is reactive to another receptor, an antigen, a chemokine and a cytokine.

9. The method of claim 1, wherein the antibody or Fc fragment is a core fucosylated or nonfucosylated IgG glycoprotein or IgG-Fc fragment comprising heterogeneous or undesired N-glycans and the method further comprises the step of:
removing the heterogeneous or undesired N-glycans by an enzyme selected from the group Endo-H, Endo-F3, Endo S or Endo-A to form the core fucosylated or nonfucosylated GlcNAc-acceptor a core homogeneous fucosylated or nonfucosylated GlcNAc-IgG acceptor.

10. The method of claim 1, wherein the GlcNAc-protein acceptor is positioned on the Fc region of the antibody.

* * * * *